(12) United States Patent
Faries et al.

(10) Patent No.: US 9,211,381 B2
(45) Date of Patent: Dec. 15, 2015

(54) METHOD AND APPARATUS FOR CONTROLLING TEMPERATURE OF MEDICAL LIQUIDS

(71) Applicant: Medical Solutions, Inc., Chantilly, VA (US)

(72) Inventors: Durward I. Faries, Las Vegas, NV (US); Tarry Ann Faries, Las Vegas, NV (US); Bruce R. Heymann, Vienna, VA (US); David Davis, Herndon, VA (US); Ray Tsang, Herndon, VA (US)

(73) Assignee: Medical Solutions, Inc., Chantilly, VA (US)

( * ) Notice: Subject to any disclaimer, the term of this patent is extended or adjusted under 35 U.S.C. 154(b) by 0 days.

(21) Appl. No.: 13/745,990

(22) Filed: Jan. 21, 2013

(65) Prior Publication Data

US 2013/0197437 A1  Aug. 1, 2013

Related U.S. Application Data

(60) Provisional application No. 61/588,767, filed on Jan. 20, 2012.

(51) Int. Cl.
*A61M 5/44* (2006.01)

(52) U.S. Cl.
CPC ......... *A61M 5/44* (2013.01); *A61M 2205/3368* (2013.01); *A61M 2205/36* (2013.01)

(58) Field of Classification Search
CPC .......... A61M 1/369; A61M 2205/127; A61M 2205/3368; A61M 2205/3372; A61M 2205/3653; A61M 5/44; A61M 2205/36
USPC .................................................. 604/113, 114
See application file for complete search history.

(56) References Cited

U.S. PATENT DOCUMENTS 522,866 A   7/1894  Weinhagen et al.
558,979 A   4/1896  Noble
(Continued)

FOREIGN PATENT DOCUMENTS

DE   3742927 A1    7/1989
DE   19752578 A1   6/1999
(Continued)

OTHER PUBLICATIONS

Health Devices, vol. 25, No. 10, Oct. 1996.
(Continued)

*Primary Examiner* — Theodore Stigell
*Assistant Examiner* — Benjamin Koo
(74) *Attorney, Agent, or Firm* — Edell, Shapiro & Finnan, LLC

(57) ABSTRACT

A system for controlling temperature of intravenous fluids includes a thermal treatment device and a temperature sensing device to measure a temperature of the fluid flowing through the sensor. The temperature sensing device may simultaneously collect two temperature measurements. For example, the sensing device may include sensors that measure the temperature of the fluid at two disparate locations along the medical fluid line. Additionally, the sensors may measure the temperature of the fluid within the medical fluid line, as well as the ambient temperature outside of the line. The thermal treatment device includes a conduit configured to have a nonlinear flow path through the device. The thermal treatment device thermally treats fluid within the conduit to a desired temperature or range.

14 Claims, 17 Drawing Sheets

(56) References Cited

U.S. PATENT DOCUMENTS

| | | |
|---|---|---|
| 675,647 A | 6/1901 | Andersen et al. |
| 785,524 A | 3/1905 | Shea |
| 803,352 A | 10/1905 | Meyer |
| 1,062,111 A | 5/1913 | Nylander |
| 1,092,643 A | 4/1914 | Goolsby |
| 1,110,919 A | 9/1914 | Gamble |
| 1,223,274 A | 4/1917 | Hallock |
| 1,390,500 A | 9/1921 | Christian |
| 1,479,451 A | 1/1924 | Buckstein |
| 1,493,450 A | 5/1924 | Richardson |
| 1,659,719 A | 2/1928 | Blake |
| 1,726,212 A | 8/1929 | Bucky |
| 1,770,832 A | 7/1930 | Bass |
| 1,794,215 A | 2/1931 | Titus |
| 1,838,026 A | 12/1931 | Williams |
| 1,847,573 A | 3/1932 | Rupp |
| 1,847,954 A | 3/1932 | Fisher |
| 1,960,417 A | 5/1934 | Pain, Jr. |
| 1,982,213 A | 11/1934 | Hopkins |
| 1,987,119 A | 1/1935 | Long |
| 1,995,302 A | 3/1935 | Goldstein |
| 2,063,902 A | 12/1936 | Beasley |
| 2,087,586 A | 7/1937 | Tishman |
| 2,124,293 A | 7/1938 | Goldstein |
| 2,175,099 A | 10/1939 | C.W. Abbott |
| 2,204,764 A | 6/1940 | Mayo |
| 2,214,215 A | 9/1940 | Watermann et al. |
| 2,254,994 A | 9/1941 | Butland |
| 2,357,692 A | 9/1944 | Saffady |
| 2,470,481 A | 5/1949 | Freeman |
| 2,576,874 A | 11/1951 | Acton |
| 2,701,789 A | 2/1955 | White |
| 2,713,112 A | 7/1955 | Mills et al. |
| 2,741,099 A | 4/1956 | Beane |
| 2,766,907 A | 10/1956 | Wallace, Jr. |
| 2,841,132 A | 7/1958 | Philipp |
| 2,880,764 A | 4/1959 | Pelavin |
| 2,885,526 A | 5/1959 | Paulding |
| 2,910,981 A | 11/1959 | Wilson et al. |
| 2,990,875 A | 7/1961 | Samuels et al. |
| 2,994,760 A | 8/1961 | Pecoraro et al. |
| 3,051,582 A | 8/1962 | Muckler et al. |
| 3,140,716 A | 7/1964 | Harrison et al. |
| 3,157,727 A | 11/1964 | Hardy et al. |
| 3,193,339 A | 7/1965 | Cooper |
| 3,241,603 A | 3/1966 | Nagata |
| 3,247,851 A | 4/1966 | Seibert |
| 3,255,812 A | 6/1966 | Bayane et al. |
| 3,293,868 A | 12/1966 | Gonzalez |
| 3,329,202 A | 7/1967 | Birman |
| 3,353,589 A | 11/1967 | Tope et al. |
| 3,370,153 A | 2/1968 | Du Fresne et al. |
| 3,386,498 A | 6/1968 | Funfstuck |
| 3,475,590 A | 10/1969 | Pins |
| 3,485,245 A * | 12/1969 | Lahr et al. .................... 604/114 |
| 3,500,366 A | 3/1970 | Chesney et al. |
| 3,536,132 A | 10/1970 | Pecoraro et al. |
| 3,551,641 A | 12/1970 | Truhan |
| 3,563,090 A | 2/1971 | Deltour |
| 3,590,215 A | 6/1971 | Anderson et al. |
| 3,591,290 A | 7/1971 | Zinner et al. |
| 3,596,515 A | 8/1971 | Cramer |
| 3,612,059 A | 10/1971 | Ersek |
| 3,612,165 A | 10/1971 | Haynes |
| 3,614,385 A | 10/1971 | Horstmann |
| 3,629,552 A | 12/1971 | Edging |
| 3,640,277 A | 2/1972 | Adelberg |
| 3,651,695 A | 3/1972 | Brown |
| 3,704,625 A | 12/1972 | Seto et al. |
| 3,713,302 A | 1/1973 | Reviel |
| 3,777,187 A | 12/1973 | Kohn |
| 3,801,278 A | 4/1974 | Wagner et al. |
| 3,826,305 A | 7/1974 | Fishman |
| 3,858,106 A | 12/1974 | Launius |
| 3,861,213 A | 1/1975 | Parker |
| 3,864,976 A | 2/1975 | Parker |
| 3,879,171 A | 4/1975 | Tulis |
| 3,895,741 A | 7/1975 | Nugent |
| 3,908,652 A | 9/1975 | Weissinger |
| 3,940,742 A | 2/1976 | Hudspeth et al. |
| 4,024,377 A | 5/1977 | Henke |
| 4,038,519 A | 7/1977 | Foucras |
| 4,063,551 A | 12/1977 | Sweeney |
| 4,084,080 A | 4/1978 | McMahan |
| 4,090,514 A | 5/1978 | Hinck et al. |
| 4,098,123 A | 7/1978 | Granzow, Jr. |
| 4,167,663 A | 9/1979 | Granzow, Jr. et al. |
| 4,189,995 A | 2/1980 | Lohr et al. |
| 4,233,495 A | 11/1980 | Scoville et al. |
| 4,293,762 A | 10/1981 | Ogawa |
| 4,309,592 A | 1/1982 | Le Boeuf |
| 4,314,484 A | 2/1982 | Bowman |
| 4,318,276 A | 3/1982 | Sato et al. |
| 4,328,676 A | 5/1982 | Reed |
| 4,331,859 A | 5/1982 | Thomas et al. |
| 4,336,435 A | 6/1982 | Kashyap et al. |
| 4,356,383 A | 10/1982 | Dahlberg et al. |
| 4,364,234 A | 12/1982 | Reed |
| 4,375,813 A | 3/1983 | Hessel |
| 4,384,578 A | 5/1983 | Winkler |
| 4,397,648 A | 8/1983 | Knute |
| 4,407,133 A | 10/1983 | Edmonson |
| 4,408,905 A | 10/1983 | Ehrenkranz |
| 4,419,568 A | 12/1983 | VanOverloop |
| 4,430,077 A | 2/1984 | Mittleman et al. |
| 4,430,078 A | 2/1984 | Sprague |
| 4,432,761 A | 2/1984 | Dawe |
| 4,448,204 A | 5/1984 | Lichtenstein |
| 4,455,478 A | 6/1984 | Guibert |
| 4,464,563 A | 8/1984 | Jewett |
| 4,468,137 A | 8/1984 | Hilsum et al. |
| 4,476,877 A | 10/1984 | Barker |
| 4,481,410 A | 11/1984 | Bortnik |
| 4,490,884 A | 1/1985 | Vickers |
| 4,495,402 A | 1/1985 | Burdick et al. |
| 4,498,901 A | 2/1985 | Finch |
| 4,509,532 A | 4/1985 | DeVries |
| 4,509,943 A | 4/1985 | Hanzawa |
| 4,522,308 A | 6/1985 | Sullivan |
| 4,523,078 A | 6/1985 | Lehmann |
| 4,529,309 A | 7/1985 | Pettersson et al. |
| 4,531,941 A | 7/1985 | Zasuwa |
| 4,532,414 A | 7/1985 | Shah et al. |
| 4,533,350 A | 8/1985 | Danby et al. |
| 4,551,136 A | 11/1985 | Mandl |
| 4,552,277 A | 11/1985 | Richardson et al. |
| 4,572,536 A | 2/1986 | Doughty |
| 4,585,441 A | 4/1986 | Archibald |
| 4,586,691 A | 5/1986 | Kozlow |
| 4,605,840 A | 8/1986 | Koopman |
| 4,613,327 A | 9/1986 | Tegrarian et al. |
| 4,614,514 A | 9/1986 | Carr et al. |
| 4,625,086 A | 11/1986 | Karino |
| 4,626,243 A | 12/1986 | Singh et al. |
| 4,628,186 A | 12/1986 | Bergemann et al. |
| 4,634,432 A | 1/1987 | Kocak |
| 4,647,756 A | 3/1987 | Willis |
| 4,651,813 A | 3/1987 | Witt et al. |
| 4,657,004 A | 4/1987 | Coffey |
| 4,673,820 A | 6/1987 | Kamen |
| 4,674,977 A | 6/1987 | Hoselton |
| 4,678,460 A | 7/1987 | Rosner |
| 4,680,445 A | 7/1987 | Ogawa |
| 4,680,977 A | 7/1987 | Conero et al. |
| 4,682,979 A | 7/1987 | Girouard |
| 4,684,367 A | 8/1987 | Schaffer et al. |
| 4,705,505 A | 11/1987 | Fried |
| 4,707,587 A | 11/1987 | Greenblatt |
| 4,709,135 A | 11/1987 | Dietrich et al. |
| 4,718,896 A | 1/1988 | Arndt et al. |
| 4,726,193 A | 2/1988 | Burke et al. |
| 4,735,609 A | 4/1988 | Comeau et al. |
| 4,745,248 A | 5/1988 | Hayes |
| 4,747,450 A | 5/1988 | Ikegame et al. |

(56) References Cited

U.S. PATENT DOCUMENTS

| | | |
|---|---|---|
| 4,747,826 A | 5/1988 | Sassano |
| 4,756,299 A | 7/1988 | Podella |
| 4,759,749 A | 7/1988 | Verkaart |
| 4,772,778 A | 9/1988 | Ogawa |
| 4,781,548 A | 11/1988 | Alderson et al. |
| 4,782,212 A | 11/1988 | Bakke |
| 4,801,777 A | 1/1989 | Auerbach |
| 4,804,367 A | 2/1989 | Smith et al. |
| 4,808,159 A | 2/1989 | Wilson |
| 4,823,554 A | 4/1989 | Trachtenberg et al. |
| 4,823,833 A | 4/1989 | Hogan et al. |
| 4,832,689 A | 5/1989 | Mauerer et al. |
| 4,844,074 A | 7/1989 | Kurucz |
| 4,844,397 A | 7/1989 | Skakoon et al. |
| 4,847,470 A | 7/1989 | Bakke |
| 4,859,360 A | 8/1989 | Suzuki et al. |
| 4,874,033 A | 10/1989 | Chatelain et al. |
| 4,874,359 A | 10/1989 | White et al. |
| 4,878,537 A | 11/1989 | Verkaart |
| 4,878,588 A | 11/1989 | Ephraim |
| 4,883,117 A | 11/1989 | Dobbs et al. |
| 4,894,207 A | 1/1990 | Archer et al. |
| 4,900,308 A | 2/1990 | Verkaart |
| 4,904,848 A | 2/1990 | Colevas |
| 4,906,816 A | 3/1990 | Van Leerdam |
| 4,910,386 A | 3/1990 | Johnson |
| 4,916,386 A | 4/1990 | Schulz |
| 4,923,681 A | 5/1990 | Cox et al. |
| 4,934,152 A | 6/1990 | Templeton |
| 4,934,336 A | 6/1990 | White |
| 4,935,604 A | 6/1990 | Allen et al. |
| 4,936,828 A | 6/1990 | Chiang |
| 4,961,320 A | 10/1990 | Gutmann |
| 4,991,976 A | 2/1991 | Byles |
| 4,994,021 A | 2/1991 | Smith et al. |
| 5,000,581 A | 3/1991 | Yata et al. |
| 5,013,889 A | 5/1991 | Bakke |
| 5,019,047 A | 5/1991 | Kriesel |
| 5,040,380 A | 8/1991 | Gregory |
| 5,042,455 A | 8/1991 | Yue et al. |
| 5,059,182 A | 10/1991 | Laing |
| 5,061,241 A | 10/1991 | Stephens, Jr. et al. |
| 5,061,630 A | 10/1991 | Knopf et al. |
| 5,063,994 A | 11/1991 | Verkaart |
| 5,073,167 A | 12/1991 | Carr et al. |
| 5,074,658 A | 12/1991 | Talvarides et al. |
| 5,075,167 A | 12/1991 | Yamauchi et al. |
| 5,081,697 A | 1/1992 | Manella |
| 5,096,078 A | 3/1992 | McQueeny |
| 5,096,822 A | 3/1992 | Rosenkrans, Jr. et al. |
| 5,097,898 A | 3/1992 | Verkaart |
| 5,103,817 A | 4/1992 | Reisdorf et al. |
| 5,106,373 A | 4/1992 | Augustine et al. |
| 5,108,372 A | 4/1992 | Swenson |
| 5,125,069 A | 6/1992 | O'Boyle |
| 5,125,900 A | 6/1992 | Teves |
| 5,129,033 A | 7/1992 | Ferrara et al. |
| 5,152,755 A | 10/1992 | Yoshinori |
| 5,153,827 A | 10/1992 | Coutre et al. |
| 5,169,389 A | 12/1992 | Kriesel |
| 5,180,896 A | 1/1993 | Gibby et al. |
| 5,183,994 A | 2/1993 | Bowles, Sr. et al. |
| 5,184,613 A | 2/1993 | Mintz |
| 5,186,057 A | 2/1993 | Everhart |
| 5,195,976 A | 3/1993 | Swenson |
| 5,205,820 A | 4/1993 | Kriesel |
| 5,211,631 A | 5/1993 | Sheaff |
| 5,217,064 A | 6/1993 | Kellow et al. |
| 5,232,439 A | 8/1993 | Campbell et al. |
| 5,241,951 A | 9/1993 | Mason et al. |
| 5,243,172 A | 9/1993 | Hazan et al. |
| 5,243,833 A | 9/1993 | Coelho et al. |
| 5,245,693 A | 9/1993 | Ford et al. |
| 5,250,032 A | 10/1993 | Carter, Jr. et al. |
| 5,254,094 A | 10/1993 | Starkey et al. |
| 5,261,411 A | 11/1993 | Hughes |
| 5,261,875 A | 11/1993 | Spears |
| 5,263,323 A | 11/1993 | Maus et al. |
| 5,263,929 A | 11/1993 | Falcone et al. |
| 5,269,749 A | 12/1993 | Koturov |
| 5,276,310 A | 1/1994 | Schmidt et al. |
| 5,279,558 A | 1/1994 | Kriesel |
| 5,279,598 A | 1/1994 | Sheaff |
| 5,282,264 A | 1/1994 | Reeves et al. |
| 5,282,683 A | 2/1994 | Brett |
| 5,290,222 A | 3/1994 | Feng et al. |
| 5,290,230 A | 3/1994 | Ainsworth et al. |
| 5,296,684 A | 3/1994 | Essig et al. |
| 5,297,234 A | 3/1994 | Harms et al. |
| 5,308,335 A | 5/1994 | Ross et al. |
| 5,315,830 A | 5/1994 | Doke et al. |
| 5,318,540 A | 6/1994 | Athayde et al. |
| 5,330,431 A | 7/1994 | Herskowitz |
| 5,333,326 A | 8/1994 | Faries, Jr. et al. |
| 5,338,157 A | 8/1994 | Blomquist |
| 5,342,313 A | 8/1994 | Campbell et al. |
| 5,345,923 A | 9/1994 | Luebke et al. |
| 5,348,539 A | 9/1994 | Herskowitz |
| 5,364,371 A | 11/1994 | Kamen |
| 5,364,385 A | 11/1994 | Harms et al. |
| 5,370,674 A | 12/1994 | Farrell |
| 5,381,510 A | 1/1995 | Ford et al. |
| 5,389,078 A | 2/1995 | Zalesky et al. |
| 5,392,025 A | 2/1995 | Figh et al. |
| 5,397,875 A | 3/1995 | Bechtold, Jr. |
| 5,399,007 A | 3/1995 | Marconet |
| 5,399,166 A | 3/1995 | Laing |
| 5,408,576 A | 4/1995 | Bishop |
| 5,408,577 A | 4/1995 | Weber, Jr. et al. |
| 5,411,480 A | 5/1995 | Kriesel |
| 5,411,482 A | 5/1995 | Campbell |
| 5,415,282 A | 5/1995 | Kienholz |
| 5,417,274 A | 5/1995 | Verkaart |
| 5,420,962 A | 5/1995 | Bakke |
| 5,423,759 A | 6/1995 | Campbell |
| 5,424,512 A | 6/1995 | Turetta et al. |
| 5,433,704 A | 7/1995 | Ross et al. |
| 5,451,209 A | 9/1995 | Ainsworth et al. |
| 5,474,538 A | 12/1995 | Stihler et al. |
| 5,482,373 A | 1/1996 | Hutchinson |
| 5,483,799 A | 1/1996 | Dalto |
| 5,485,408 A | 1/1996 | Blomquist |
| 5,492,534 A | 2/1996 | Athayde et al. |
| 5,494,196 A | 2/1996 | Tyner |
| 5,512,043 A | 4/1996 | Verkaart |
| 5,514,095 A | 5/1996 | Brightbill et al. |
| 5,523,055 A | 6/1996 | Hansen et al. |
| 5,531,697 A | 7/1996 | Olsen et al. |
| 5,531,698 A | 7/1996 | Olsen |
| 5,538,399 A | 7/1996 | Johnson |
| 5,540,561 A | 7/1996 | Johnson |
| 5,564,915 A | 10/1996 | Johnson |
| 5,567,119 A | 10/1996 | Johnson |
| 5,567,136 A | 10/1996 | Johnson |
| 5,572,873 A | 11/1996 | Lavigne et al. |
| 5,575,563 A | 11/1996 | Chiu et al. |
| 5,584,811 A | 12/1996 | Ross et al. |
| 5,590,648 A | 1/1997 | Mitchell et al. |
| 5,609,784 A | 3/1997 | Davenport |
| RE35,501 E | 5/1997 | Ross et al. |
| 5,634,426 A | 6/1997 | Tomlinson et al. |
| 5,647,854 A | 7/1997 | Olsen et al. |
| 5,649,910 A | 7/1997 | Kriesel et al. |
| 5,653,905 A | 8/1997 | McKinney |
| 5,658,250 A | 8/1997 | Blomquist et al. |
| 5,658,252 A | 8/1997 | Johnson |
| 5,658,478 A | 8/1997 | Roeschel et al. |
| 5,661,978 A | 9/1997 | Holmes et al. |
| 5,669,877 A | 9/1997 | Blomquist |
| 5,678,925 A | 10/1997 | Garmaise et al. |
| 5,681,284 A | 10/1997 | Herskowitz |
| 5,683,381 A | 11/1997 | Carr et al. |
| 5,690,614 A | 11/1997 | Carr et al. |
| 5,695,473 A | 12/1997 | Olsen |

(56) References Cited

U.S. PATENT DOCUMENTS

| | | | |
|---|---|---|---|
| 5,707,151 A | 1/1998 | Parker et al. |
| 5,707,431 A | 1/1998 | Verkaart et al. |
| 5,713,864 A | 2/1998 | Verkaart |
| 5,720,728 A | 2/1998 | Ford |
| 5,729,653 A | 3/1998 | Magliochetti et al. |
| 5,733,263 A | 3/1998 | Wheatman |
| 5,738,442 A | 4/1998 | Paron et al. |
| 5,743,878 A | 4/1998 | Ross et al. |
| 5,744,806 A | 4/1998 | Frojd |
| 5,755,275 A | 5/1998 | Rose et al. |
| 5,772,409 A | 6/1998 | Johnson |
| 5,779,364 A | 7/1998 | Cannelongo et al. |
| 5,786,568 A | 7/1998 | McKinney |
| 5,788,669 A | 8/1998 | Peterson |
| 5,788,671 A | 8/1998 | Johnson |
| 5,805,455 A | 9/1998 | Lipps |
| 5,806,528 A | 9/1998 | Magliochetti |
| 5,807,332 A | 9/1998 | Augustine et al. |
| 5,810,771 A | 9/1998 | Blomquist |
| 5,816,797 A | 10/1998 | Shoenfeld |
| 5,817,146 A | 10/1998 | Augustine |
| 5,823,746 A | 10/1998 | Johnson |
| 5,824,000 A | 10/1998 | Pavlo et al. |
| 5,840,068 A | 11/1998 | Cartledge |
| 5,858,303 A | 1/1999 | Schiffmann et al. |
| 5,862,672 A | 1/1999 | Faries, Jr. et al. |
| 5,875,282 A | 2/1999 | Jordan et al. |
| 5,876,370 A | 3/1999 | Blomquist |
| 5,879,143 A | 3/1999 | Cote et al. |
| 5,879,329 A | 3/1999 | Ginsburg |
| 5,891,096 A | 4/1999 | Hyun et al. |
| 5,893,843 A | 4/1999 | Rodrigues |
| 5,897,207 A | 4/1999 | Hartmann |
| 5,910,210 A | 6/1999 | Violi et al. |
| 5,919,218 A | 7/1999 | Carr |
| 5,924,289 A | 7/1999 | Bishop, II |
| 5,928,196 A | 7/1999 | Johnson et al. |
| 5,935,099 A | 8/1999 | Peterson et al. |
| 5,935,106 A | 8/1999 | Olsen |
| 5,954,485 A | 9/1999 | Johnson et al. |
| 5,954,700 A | 9/1999 | Kovelman |
| 5,961,492 A | 10/1999 | Kriesel et al. |
| 5,961,700 A | 10/1999 | Oliver |
| 5,961,866 A | 10/1999 | Hansen |
| 5,977,520 A | 11/1999 | Madson, Jr. et al. |
| 5,986,239 A | 11/1999 | Corrigan, III |
| 5,989,238 A | 11/1999 | Ginsburg |
| 5,997,927 A | 12/1999 | Gics |
| 6,024,539 A | 2/2000 | Blomquist |
| 6,035,102 A | 3/2000 | Bakke |
| 6,039,926 A | 3/2000 | Goldman |
| 6,045,648 A | 4/2000 | Palmgren et al. |
| 6,062,429 A | 5/2000 | West et al. |
| 6,096,007 A | 8/2000 | Haan et al. |
| 6,117,122 A | 9/2000 | Din et al. |
| 6,123,827 A | 9/2000 | Wong et al. |
| 6,124,572 A | 9/2000 | Spilger et al. |
| 6,129,702 A | 10/2000 | Woias et al. |
| 6,139,528 A | 10/2000 | Kristner et al. |
| 6,142,974 A | 11/2000 | Kristner et al. |
| 6,146,359 A | 11/2000 | Carr et al. |
| 6,158,458 A | 12/2000 | Ryan |
| 6,164,469 A | 12/2000 | Sartore |
| 6,174,300 B1 | 1/2001 | Kriesel et al. |
| 6,175,099 B1 | 1/2001 | Shei et al. |
| 6,175,688 B1 | 1/2001 | Cassidy et al. |
| 6,221,045 B1 | 4/2001 | Duchon et al. |
| 6,221,051 B1 | 4/2001 | Hjertman et al. |
| 6,248,077 B1 | 6/2001 | Elson et al. |
| 6,254,572 B1 | 7/2001 | Knipfer et al. |
| 6,257,759 B1 | 7/2001 | Witonsky et al. |
| 6,259,067 B1 | 7/2001 | Faries, Jr. et al. |
| 6,261,261 B1 | 7/2001 | Gordon |
| 6,264,049 B1 | 7/2001 | Shteynberg |
| 6,294,762 B1 | 9/2001 | Faries, Jr. et al. |
| 6,315,767 B1 | 11/2001 | Dumont et al. |
| 6,316,750 B1 | 11/2001 | Levin |
| 6,334,707 B1 | 1/2002 | Ku |
| 6,371,121 B1 | 4/2002 | Faries, Jr. et al. |
| 6,376,805 B2 | 4/2002 | Faries, Jr. et al. |
| 6,384,380 B1 | 5/2002 | Faries, Jr. et al. |
| 6,464,666 B1 | 10/2002 | Augustine |
| 6,467,953 B1 | 10/2002 | Faries, Jr. et al. |
| 6,524,239 B1 | 2/2003 | Reed et al. |
| 6,553,336 B1 | 4/2003 | Johnson et al. |
| 6,566,631 B2 | 5/2003 | Faries et al. |
| 6,607,027 B2 | 8/2003 | Bosch et al. |
| 6,641,556 B1 * | 11/2003 | Shigezawa ................... 604/113 |
| 6,641,602 B2 | 11/2003 | Balding |
| 6,649,040 B1 | 11/2003 | Mirchi et al. |
| 6,660,974 B2 | 12/2003 | Faries et al. |
| 6,722,782 B2 | 4/2004 | Faries, Jr. et al. |
| 6,736,788 B1 | 5/2004 | Mongomery et al. |
| 6,740,059 B2 | 5/2004 | Flaherty |
| 6,748,164 B1 | 6/2004 | Kuzyk |
| 6,768,085 B2 | 7/2004 | Faries et al. |
| 6,788,885 B2 | 9/2004 | Mitsunaga |
| 6,788,997 B1 | 9/2004 | Frederick |
| 6,824,528 B1 | 11/2004 | Faries, Jr. et al. |
| 6,850,252 B1 | 2/2005 | Hoffberg |
| 6,860,271 B2 | 3/2005 | Faries, Jr. et al. |
| 6,869,538 B2 | 3/2005 | Yu et al. |
| 6,967,575 B1 | 11/2005 | Dohrmann et al. |
| 7,031,602 B2 | 4/2006 | Faries, Jr. et al. |
| 7,031,778 B2 | 4/2006 | Hsiung et al. |
| 7,041,941 B2 | 5/2006 | Faries, Jr. et al. |
| 7,090,658 B2 | 8/2006 | Faries, Jr. et al. |
| 7,176,030 B2 | 2/2007 | Faries, Jr. et al. |
| 7,238,171 B2 | 7/2007 | Faries, Jr. et al. |
| 7,262,698 B1 | 8/2007 | Frederick et al. |
| 7,276,675 B2 | 10/2007 | Faries, Jr. et al. |
| 7,307,245 B2 | 12/2007 | Faries, Jr. et al. |
| 7,326,882 B2 | 2/2008 | Faries, Jr. et al. |
| 7,417,205 B2 | 8/2008 | Faries, Jr. et al. |
| 7,540,864 B2 | 6/2009 | Faries, Jr. et al. |
| 7,608,460 B2 | 10/2009 | Reed et al. |
| 7,611,504 B1 | 11/2009 | Faries, Jr. et al. |
| 7,726,876 B2 | 6/2010 | Laverdiere et al. |
| 7,740,611 B2 | 6/2010 | Faries, Jr. et al. |
| 7,942,851 B2 | 5/2011 | Faries, Jr. et al. |
| 8,226,293 B2 | 7/2012 | Faries, Jr. et al. |
| 8,226,605 B2 | 7/2012 | Faries, Jr. et al. |
| 8,313,462 B2 | 11/2012 | Faries, Jr. |
| 8,444,599 B2 | 5/2013 | Faries, Jr. et al. |
| 8,487,738 B2 | 7/2013 | Faries, Jr. et al. |
| 8,636,691 B2 | 1/2014 | Faries, Jr. |
| 8,734,404 B2 | 5/2014 | Faries, Jr. |
| 8,734,405 B2 | 5/2014 | Faries, Jr. |
| 8,821,011 B2 | 9/2014 | Faries, Jr. et al. |
| 8,845,586 B2 | 9/2014 | Faries, Jr. et al. |
| 8,920,372 B2 | 12/2014 | Faries, Jr. et al. |
| 8,920,387 B2 | 12/2014 | Faries, Jr. et al. |
| 2001/0009610 A1 | 7/2001 | Augustine et al. |
| 2002/0081109 A1 | 6/2002 | Mitsunaga et al. |
| 2002/0147426 A1 | 10/2002 | Faries, Jr. et al. |
| 2002/0151854 A1 | 10/2002 | Duchon et al. |
| 2002/0156451 A1 | 10/2002 | Lenker |
| 2002/0158058 A1 | 10/2002 | Faries, Jr. et al. |
| 2002/0184906 A1 | 12/2002 | Faries, Jr. et al. |
| 2003/0000939 A1 | 1/2003 | Faries et al. |
| 2003/0004470 A1 | 1/2003 | Hickerson et al. |
| 2003/0114795 A1 | 6/2003 | Faries, Jr. et al. |
| 2003/0135388 A1 | 7/2003 | Martucci et al. |
| 2003/0216831 A1 | 11/2003 | Hart et al. |
| 2003/0218003 A1 | 11/2003 | Ellis et al. |
| 2003/0222933 A1 | 12/2003 | Choi |
| 2004/0170409 A1 | 9/2004 | Faries, Jr. et al. |
| 2004/0189258 A1 | 9/2004 | Lehmann et al. |
| 2004/0247016 A1 | 12/2004 | Faries, Jr. et al. |
| 2005/0059952 A1 | 3/2005 | Giuliano et al. |
| 2005/0070845 A1 | 3/2005 | Faries, Jr. et al. |
| 2005/0142013 A1 | 6/2005 | Faries, Jr. et al. |
| 2005/0222933 A1 | 10/2005 | Wesby |
| 2005/0242930 A1 | 11/2005 | Nicolson et al. |

(56) References Cited

U.S. PATENT DOCUMENTS

| | | |
|---|---|---|
| 2006/0020255 A1 | 1/2006 | Cassidy et al. |
| 2006/0100578 A1 | 5/2006 | Lieberman |
| 2006/0253075 A1 | 11/2006 | Faries, Jr. et al. |
| 2006/0291533 A1 | 12/2006 | Faries, Jr. et al. |
| 2007/0000910 A1 | 1/2007 | Faries, Jr. et al. |
| 2007/0015975 A1 | 1/2007 | Faries, Jr. et al. |
| 2007/0106243 A1 | 5/2007 | Faries, Jr. et al. |
| 2007/0142773 A1 | 6/2007 | Rosiello et al. |
| 2007/0161952 A1 | 7/2007 | Faries, Jr. et al. |
| 2007/0215018 A1 | 9/2007 | Faries, Jr. et al. |
| 2008/0021392 A1 | 1/2008 | Lurvey et al. |
| 2008/0058697 A1* | 3/2008 | Kamen et al. .......... 604/6.13 |
| 2008/0147016 A1 | 6/2008 | Faries et al. |
| 2008/0205481 A1 | 8/2008 | Faries et al. |
| 2010/0059498 A1 | 3/2010 | Hansen et al. |
| 2010/0082459 A1 | 4/2010 | Tusa et al. |
| 2010/0111135 A1 | 5/2010 | Faries, Jr. et al. |
| 2010/0168671 A1 | 7/2010 | Faries, Jr. et al. |
| 2010/0222762 A1 | 9/2010 | Faries, Jr. et al. |
| 2010/0222763 A1 | 9/2010 | Faries, Jr. et al. |
| 2011/0297831 A1 | 12/2011 | Yao et al. |
| 2011/0307274 A1 | 12/2011 | Thompson et al. |
| 2012/0053518 A1 | 3/2012 | Faries, Jr. et al. |
| 2012/0191050 A1 | 7/2012 | Faries, Jr. et al. |
| 2012/0265336 A1 | 10/2012 | Mallet et al. |
| 2012/0285236 A1* | 11/2012 | Haartsen et al. .......... 73/204.11 |
| 2013/0197437 A1 | 8/2013 | Faries et al. |
| 2013/0253952 A1 | 9/2013 | Burke et al. |
| 2014/0231406 A1 | 8/2014 | Tsang et al. |
| 2014/0236615 A1 | 8/2014 | Ragusky et al. |

FOREIGN PATENT DOCUMENTS

| | | |
|---|---|---|
| EP | 0927552 A1 | 7/1999 |
| GB | 2029677 A | 3/1980 |
| GB | 2274514 | 7/1994 |
| JP | 58-030666 | 2/1983 |
| JP | 2000-300666 | 10/2000 |
| NZ | 331678 A | 3/2000 |
| WO | 9221272 | 12/1992 |
| WO | 98/38953 A1 | 9/1998 |
| WO | 98/45658 A1 | 10/1998 |
| WO | 9845658 | 10/1998 |
| WO | 99/22786 A1 | 5/1999 |
| WO | 99/58177 A1 | 11/1999 |

OTHER PUBLICATIONS

Minco Products, Inc., Bulletin CT198, 1996.

Eurotherm Controls, Inc., Model 2116 Temperature Controller, 1997.

Ellenwood, Drop Detector, IBM Technical Bulletin, vol. 12, No. 5, Oct. 1969.

Cbi Medical, Inc., IV Fluid Warmer Model 8362, 1992.

Cahill, New Name, New Helmsman, JEMS, Aug. 1996.

Cbi Healthcare Systems, Inc. Controlled Temperature Cabinet Syste, JEMS, Mar. 17, 1997.

Koolatron, P-34 PC-3 Precision Control Thermolectric Cooler/Warmer, Jan. 1998.

Koolatron, Canadian Company announces the release of a precision control unit, Aug. 1997.

Anton, 500 miles from nowhere, it'll give you a cold drink or a warm burger . . . , Technology Update, 1993.

Koolatron, 1997 U.S. $Price List, 1997.

Kellow et al, Drug Adulteration in Prehospital Emergency Medical Services, Oct. 1994.

PCT International Search Report and Written Opinion, PCT/US2014/015944, Jun. 2, 2014, 11 pages.

PCT International Search Report and Written Opinion, PCT/US2014/016869, Jun. 27, 2014, 10 pages.

* cited by examiner

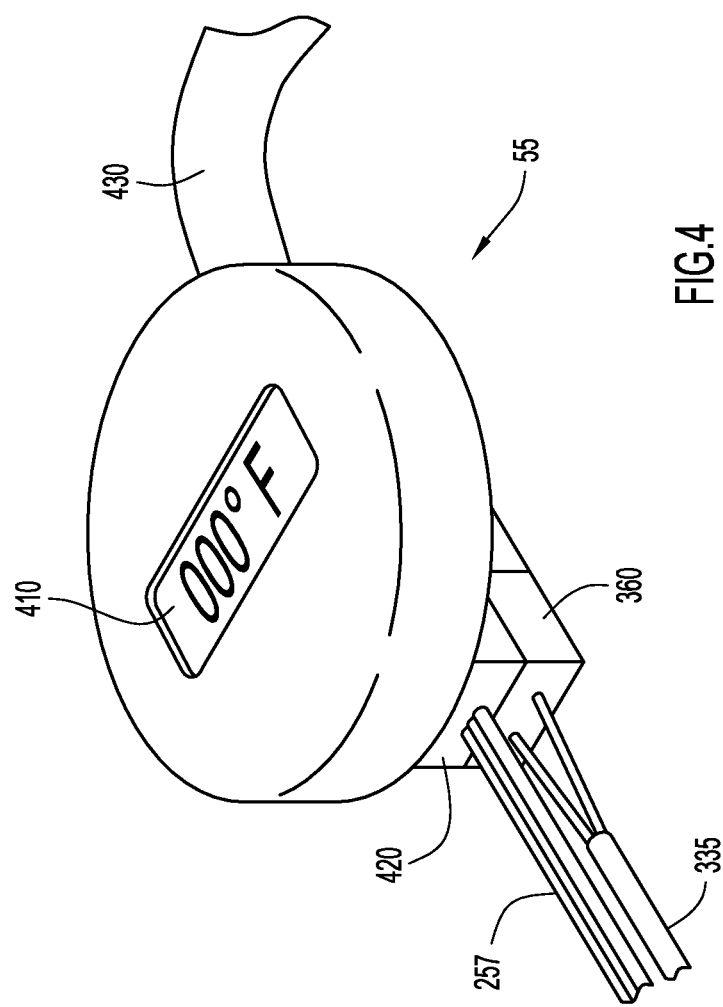

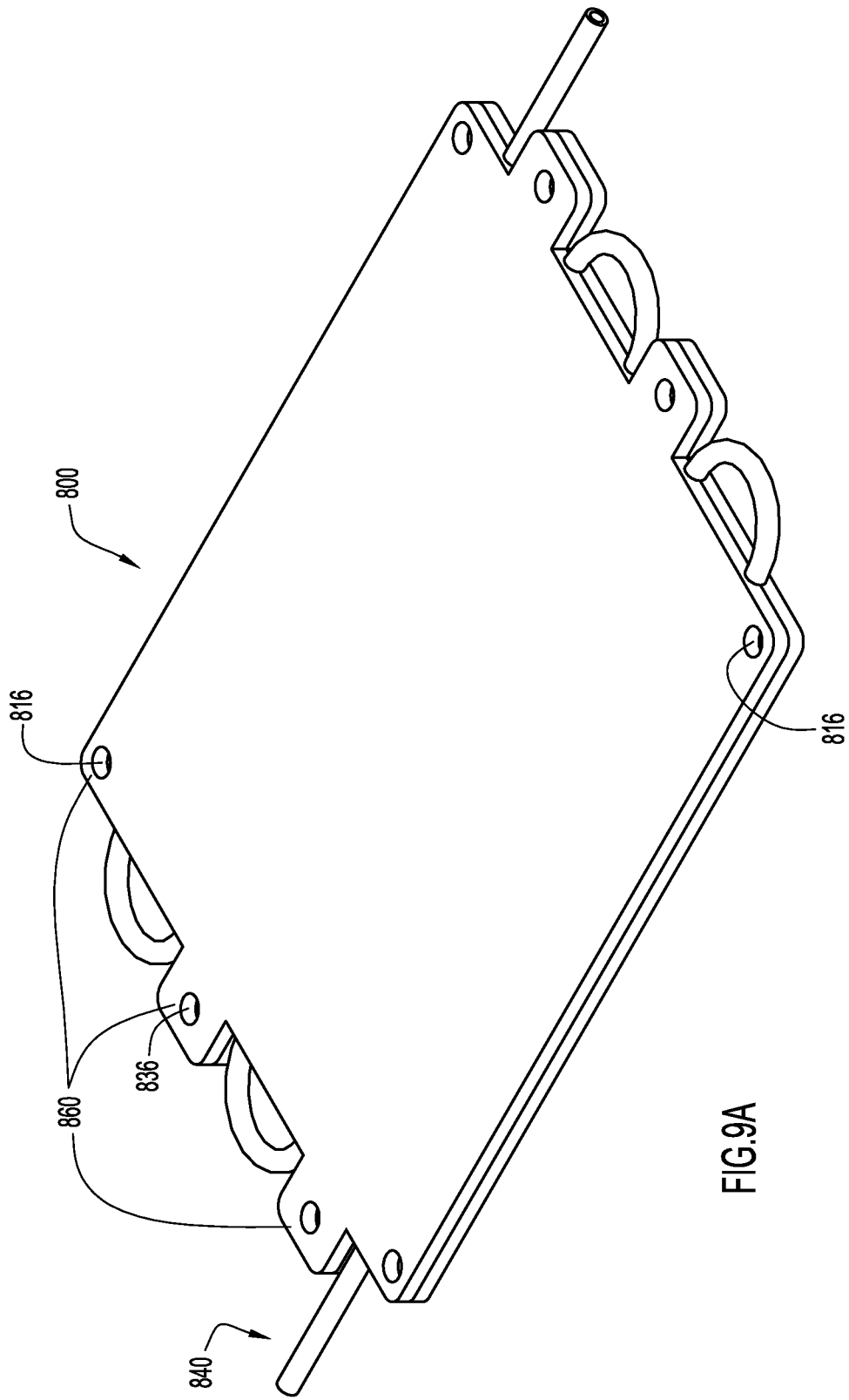

METHOD AND APPARATUS FOR CONTROLLING TEMPERATURE OF MEDICAL LIQUIDS

CROSS REFERENCE TO RELATED APPLICATIONS

This application claims priority to U.S. Provisional Patent Application Ser. No. 61/588,767, entitled "Method and Apparatus for Controlling Temperature of Medical Liquids" and filed 20 Jan. 2012, the disclosure of which is incorporated herein by reference in its entirety.

FIELD OF THE INVENTION

The present invention embodiments pertain to temperature control systems for infused liquids. In particular, the present invention embodiments are directed toward a system that monitors and/or controls the temperature of a fluid as it travels from a container to the patient during a medical procedure.

BACKGROUND OF THE INVENTION

Generally, various items are required to be heated prior to use in a medical procedure, or in support of related medical care, to prevent injury to a patient. These items typically include intravenous solutions, irrigation fluids, surgical instruments, bottles, and blankets. Intravenous (IV) fluids, for example, are typically stored in a cool environment and, consequently, require heating to precise temperatures to prevent thermal shock and injury from occurring during infusion of the fluid into a patient. Similarly, irrigation fluids can be warmed or cooled to various temperatures depending upon their intended use. These types of fluids are typically provided to a patient utilizing a flexible bag or container filled with the fluid and delivered via a fluid line that conveys the fluid from the bag to the patient.

Some medical items can only be heated for a limited period of time, or in accordance with controlled warming cycles, in order to avoid adversely affecting their effectiveness. For example, some fluids (such as whole blood or fluids containing medication) should be warmed evenly to a specific temperature and can be rendered unusable or unsafe if all or a portion of the fluid is overheated.

Thus, it is desirable to provide a system operable to control the temperature of fluids being infused into a patient.

SUMMARY OF THE INVENTION

According to one embodiment of the present invention, a system for controlling temperature of intravenous fluids includes a heating assembly that is selectively placed along the fluid conduit directing fluid from a source to the patient. The heating assembly includes a fitting with a heating unit surrounding a portion of the fitting. The assembly further includes a temperature sensor to measure a temperature of the fluid flowing through the sensor. In one embodiment, the temperature sensor measures the temperature of the fluid at a point proximate the inlet of the sensor housing and at a point proximate the outlet of the sensor housing. In another embodiment, the temperature sensor measures the temperature of the fluid traveling through the sensor housing as well as the ambient temperature. In either embodiment, the measured temperatures are utilized to calculate ramping profiles for the heating unit. The system further includes a controller to control the heating assembly in accordance with a desired temperature entered into the controller for system operation.

In addition, an embodiment of the present invention includes a warming unit including a warming device and a cartridge. The cartridge is coupled to an infusion line and includes a removable conduit that may be sterilized prior to each use. The warming device thermally treats fluid within the conduit to a desired temperature or range.

BRIEF DESCRIPTION OF THE DRAWINGS

FIG. 4 illustrates a close-up view of an inline display unit in accordance with an embodiment of the invention.

FIG. 9A is a view in perspective of the warming device cartridge of FIG. 8 employing fasteners to secure heating plates according to an embodiment of the present invention.

Like reference numerals in the various figures are utilized to designate like components.

DESCRIPTION OF THE PREFERRED EMBODIMENTS

Figure 1A:
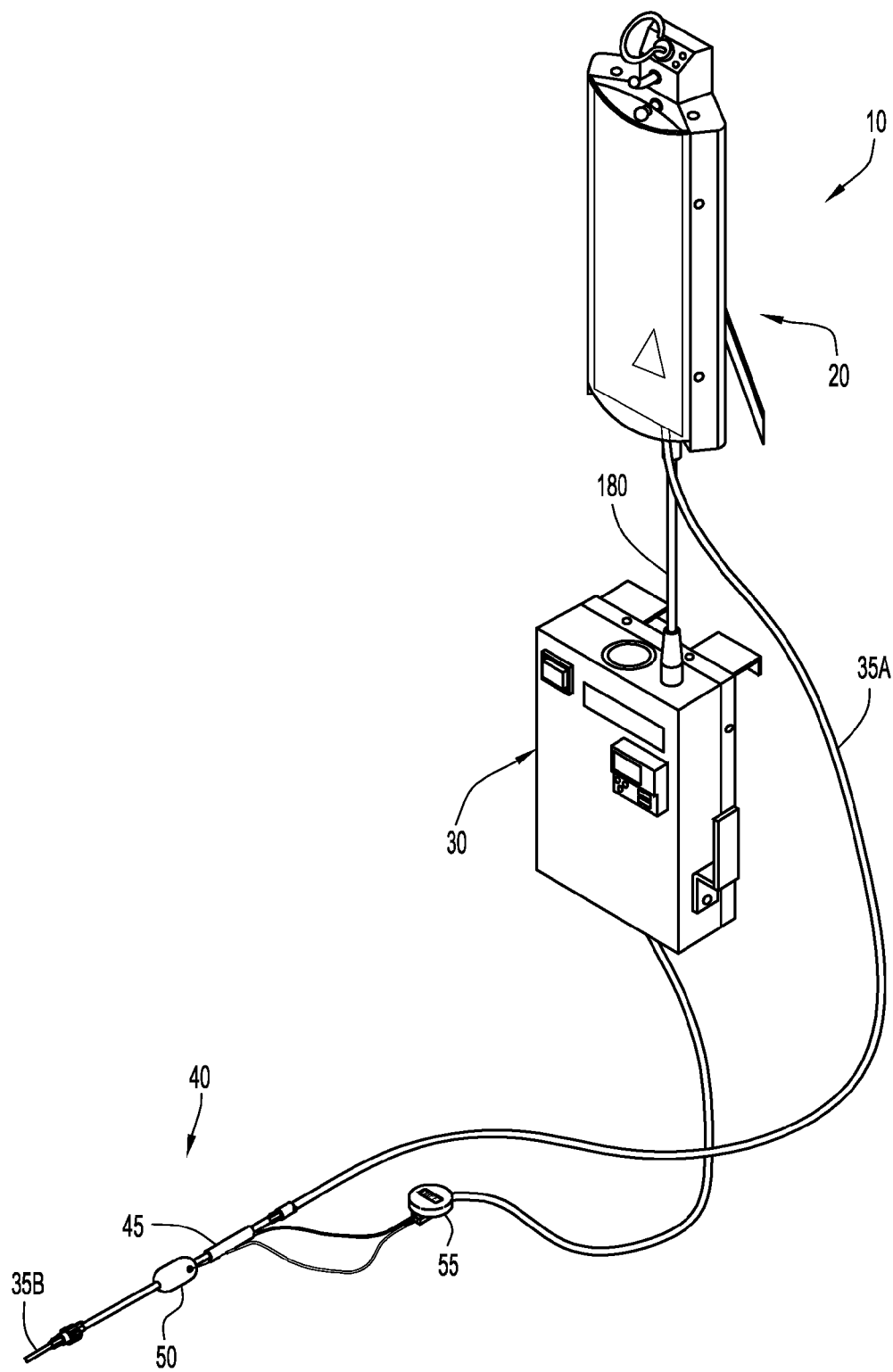
FIG. 1A illustrates a perspective view of a temperature controlled infusion system according to the present invention.
Figure 1C:
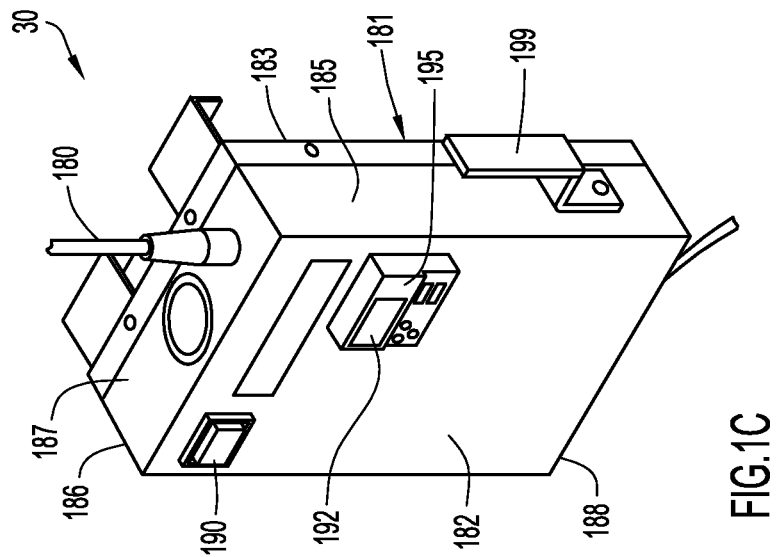
FIG. 1C illustrates a perspective view of the control cabinet in isolation.
Figure 1B:
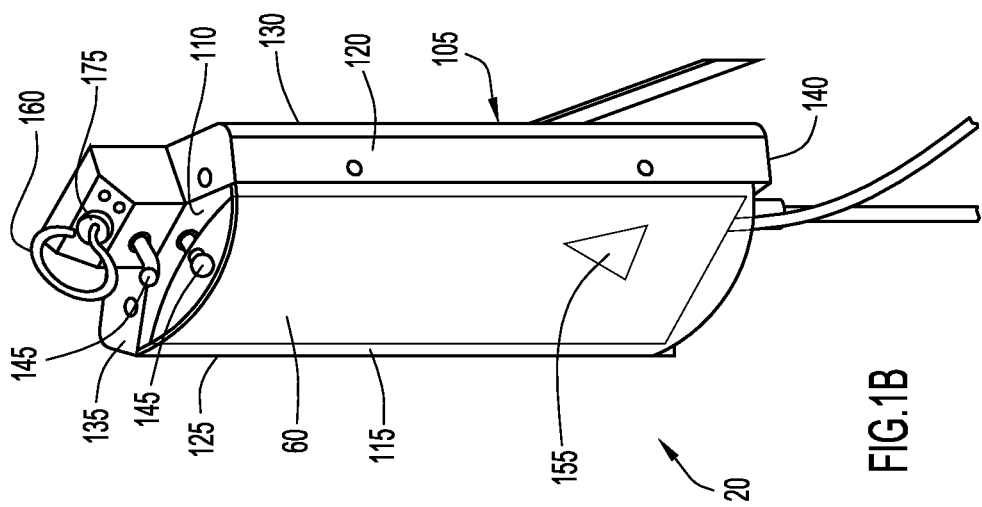
FIG. 1B illustrates a perspective view of the dispensing unit in isolation.

Referring to the embodiment illustrated in FIGS. 1A-1C, the temperature controlled infusion system 10 includes a heating cabinet 20, a temperature or power control cabinet 30, a fluid conduit, and an inline assembly 40. The fluid conduit is defined by a first fluid conduit section 35A (e.g., an IV line) disposed upstream from and in fluid communication with the inline assembly 40, and a second fluid conduit section 35B (e.g., an IV line or a medical instrument such as a catheter)

disposed downstream from and in fluid communication with the inline assembly. The inline assembly 40 may include an in-line heating unit 45, an inline temperature sensor 50, and/or an inline display unit 55. The heating cabinet 20 and/or temperature control cabinet 30 may be secured to any suitable support structure such as an IV pole, an operating table, a wall surface, a combination thereof, etc.

Referring to FIG. 1B, the heating cabinet 20 receives a solution container 60 containing the solution to be administered during the medical procedure. By way of example, the solution container 60 may be a pliable container such as an intravenous fluid bag, a blood bag, a bag including solution used for irrigation, etc. The cabinet 20 is configured for holding one or more solution containers of varying shapes and dimensions. The heating cabinet 20 includes a container receiving area defined by a housing 105, a heating plate 110 recessed within the housing, and a cover or flap 115.

The housing 105 is generally compact for easy portability. The housing 105 includes sidewalls 120, 125 extending from opposing longitudinal edges of the heating plate 110 to a rear wall 130 that is dimensioned to generally conform to the arcuate profile of the heating plate 110. Top 135 and bottom 140 walls extend between the respective upper and lower edges of the heating plate 110, housing sidewalls 120, 125, and rear wall 130, thus defining an enclosed housing interior of the heating cabinet. Extending transversely from an upper portion of heating plate 110 near top wall 135 is a hook member 145. The hook member 145 is suitably aligned on the heating plate 110 to engage an aperture in an upper portion of solution container 60 so as to secure the solution container in suitable alignment with the heating plate 110 prior to engaging the cover 115 with the solution container 60 as described below. Alternatively, the hook member 145 may be provided on the top wall 135 of the heating cabinet housing 105 or at any other suitable location to facilitate appropriate alignment of the solution container with the heating plate.

The heating plate 110 has a generally curved or arcuate configuration adapted to conform to or surround the solution container 60 and thereby evenly distribute heat to the container. The heating plate 110 is further suitably dimensioned to engage and provide heat to a variety of different sized solution containers. By way of example, the heating plate 110 may include at least one heating plate section or panel to apply heat to the solution container 60. By way of further example, the heating plate 110 includes the central or middle panel that is disposed between a lateral or side panels oriented transverse with respect to the central panel. Additional information relating to the heating panel may be found in U.S. Pat. No. 7,031,602 (Faries, Jr. et al.), the disclosure of which is incorporated herein by reference in its entirety.

The heating cabinet 20 further includes at least one heating pad disposed proximate the heating plate 110 to apply heat to at least a portion of the plate sections surrounding the solution container 60. The heating pad is preferably disposed on the interior surface of the heating plate 110 (within the interior of the housing 105) to prevent direct contact between the heating pad and the solution container 60 secured against the heating plate 110. Optionally, the heating plate 110 may include any suitable number of heating pads disposed at selected locations to provide uniform heating along the heating plate 110.

The heating plate 110 may be controlled utilizing a heater control circuit in communication with heating control elements disposed within the housing interior of the cabinet 20. The heater control circuit (described in greater detail in reference to FIG. 5) includes a heating controller and a temperature controller that serves as a safety limit switch to turn off the heating controller if a threshold temperature of the heating plate is exceeded. The heater control circuit is in communication with a temperature sensor 155 disposed within the container receiving area of the housing 105 to sense the temperature of the solution container 60. The temperature sensor 155 extends through heating plate 110 at a suitable location to facilitate direct contact with the solution container 60 secured to the heating plate. The temperature sensor 155 is preferably a resistive temperature-sensing device (e.g., a RTD sensor). However, it is noted that the temperature sensor 155 may be of any suitable type for measuring the temperature of the solution bag. Optionally, the heating control circuit may further include any suitable type of display devices (e.g., an LCD display 192 disposed on the heating cabinet housing 105) to display temperatures measured by the temperature sensor 155 and/or any suitable type of input devices 195 (e.g., buttons or keys disposed on the heating cabinet housing) to facilitate entry of a desired or set point temperature for the solution container and/or an excessive threshold temperature for the heating plate.

The heater control circuit may further include a power indicator to provide an indication that the heating cabinet 20 is receiving power from the control cabinet 30. By way of example, the power indicator may be a light emitting diode (LED) extending from the bottom wall 140 of the housing 105 of the heating cabinet 20. The LED provides an indication as to whether the heating cabinet is activated (i.e., that the heating cabinet 20 is receiving power from the control cabinet 30) to maintain the solution container 60 at the desired temperature. It is noted that the power indicator may be disposed at any suitable locations on the heating cabinet 20 and may include any suitable number and type of indication devices (e.g., an LCD display) to indicate activation of the heating cabinet.

The heating cabinet 20 may optionally include a secondary power source disposed in the cabinet housing 105 to facilitate operation of the heating cabinet in certain situations when the heating cabinet has been disconnected from the control cabinet 30. A secondary power switch may further be provided at any suitable location on the heating cabinet 20 to facilitate activation and/or deactivation of the secondary power source.

The heating cabinet 20 further includes an adjustable support member 160 to releasably support the heating cabinet 20 to a support structure during system operation (such as an IV pole or other support structure). By way of example, the support member 160 may be in the form of a ring extending from the top wall 135 of the heating cabinet housing 105. The ring 160 releasably engages with a hook support member extending transversely from an upper section of the support structure. A securing pin may connect the ring to the cabinet housing top wall 135 to permit the heating cabinet 20 to be suspended from the support structure during system operation. In particular, the securing pin may be rotationally secured within a base 175 disposed in a locking recess that is within the top wall 135 to permit full 360° rotation of the heating cabinet 20 about a central longitudinal axis of the securing pin and, as such, a variety of orientations of the heating cabinet 20 with respect to the support structure. In an exemplary embodiment, engagement of the securing pin within the base 175 may include a swivel type connection. Optionally, engagement of the securing pin and base 175 may include a ratchet-type connection, where the base includes a plurality of radially extending teeth and the securing pin includes a pawl or other suitable engaging member transversely extending from the securing pin to releasably lock between adjacent teeth of the base during rotations of the heating cabinet 20 with respect to the pin. Thus, the heating cabinet 20 may be rotated in a variety of orientations with respect to the support structure (e.g., an IV pole) so as to permit selective alignment of the front portion of the heating cabinet with respect to the position of the user or medical personnel during system operation.

The cover 115 of the heating cabinet 20 is configured to enclose (wrap around) at least a portion of solution container 60 to secure it within the housing 105. The cover 115 may be formed from any materials and possess any dimensions suitable for its described purpose. In one embodiment, the cover 115 is constructed of a substantially transparent conformable plastic material having a generally rectangular shape with a side edge secured to a first portion of housing rear wall 130. The cover 115 may be flexible and/or include a fastener operable to selectively connect the unsecured side edge to the housing 105. By way of specific example, the fastener may be a conventional hook-and-loop fastener (e.g., VELCRO) disposed on the cover interior surface toward the cover unsecured side for engagement with a corresponding mating fastener (not shown) disposed on a second portion of the housing rear wall 130 that is separated from the first portion of the housing rear wall section to which the side edge of the cover is secured. Preferably, the cover 115 is suitably dimensioned to cover all or part of the heating plate 110 when the cover is fastened to the second portion of the housing rear wall 130. The cover 115 secures the solution container 60 against the heating plate 110 to ensure uniform heating such that the solution within the container is maintained at the desired temperature during system operation.

The cover 115 may further include various devices to enhance infusion. By way of example, the cover 115 may include an inflatable bellows or bladder (not shown) disposed on the cover interior surface. The bladder applies pressure to the solution container 60 to achieve a desired solution flow or infusion rate and to force the bag against the heating plate 110 to warm the solution. The bellows is preferably coupled to a manual pump (e.g., bulb) by a tube to provide and maintain a desired pressure within the bellows to achieve a particular flow or infusion rate of solution. The pressure within the bellows may be displayed by a pressure gauge. Alternatively, the bellows may be coupled to a pump within the heating cabinet 20 or the control cabinet 30 that automatically controls pressure within the bellows in accordance with preset or user provided flow rate settings. The bellows may be secured to the cover 115 in any fashion and may be of any shape or size. For example, the upper portion of the bellows may include greater dimensions than those of the lower portion to provide a downward force against the solution bag for enhanced flow.

In addition, the cover 115 may include a cover heating element to apply heat to the front surface of the solution container 60, thereby providing heat to substantially all sides of the container 60. For example, a cover heating element may be disposed on a cover interior surface in facing relation with heating plate 110. The cover heating element is preferably implemented by a clear or transparent acrylic heater including a sheet with electrically conductive wiring embedded therein (a transparent heating element enables viewing of the solution container 60). Wiring is arranged within the sheet (and, hence, on the cover 115) to coincide with the solution container 60. By way of example, the wiring is configured as a plurality of longitudinally extending parallel lines. However, any configuration coincident the solution container 60 may be employed. The wiring further includes connection terminals disposed toward a bottom edge of sheet to connect to the heater control circuit via a wire. Alternatively, the cover heating element and/or wiring may be formed integral with cover 115.

The heating cabinet 20 may further be adapted to connect to a cable or cord to enable electrical connection and/or communication between the heating cabinet and the control cabinet 30. For example, as seen best in FIG. 1A, a connection cord 180 may operatively couple the heating cabinet 20 to the temperature control cabinet 30. By way of example, the connection cord 180 may be a power supply cord that supplies electrical power to the heating cabinet 20 during system operation. In one embodiment, disposed on bottom wall 140 of the heating cabinet housing 105 is a cable port configured to receive an end of the cord 180. The port is configured for releasable engagement with the cord 180 so as to permit disconnection of the heating cabinet 20 from the control cabinet 30 in the event that only the heating cabinet 20 is to be transported along with a patient to another location. Alternatively, the cord 180 may be permanently secured to the port of the heating cabinet 20. The heating cabinet 20 may further include a retractable cord mechanism to retract the power cord into the heating cabinet for easy storage.

Referring to FIG. 1C, the control cabinet 30 includes a generally rectangular housing 181 with a front wall 182, an opposing rear wall 183, opposing sidewalls 185, 186 and top and bottom walls 187, 188. A power control circuit (described below in relation to FIG. 5) is disposed within the interior of the housing 181 as defined by the front 182, rear 183, side 185, 186, top 187, and bottom 188 walls. The power control circuit provides power to the heating cabinet 20 during system operation. The rear wall 183 of the control cabinet 30 also includes a removable back panel to permit access to control circuit elements disposed within the control cabinet 30.

The control cabinet 30 includes a power switch 190 and display device 192 disposed on front wall 182 near the upper end of the power supply cabinet. The display device 192 may be of any suitable type (e.g., an LCD display) to provide an indication of the solution container 60 temperature measured by the temperature sensor in the heating cabinet. Input devices 195 (e.g., buttons, keys, keypad, etc.) may be disposed proximate display 192 to facilitate entry of information (e.g., set points, thresholds, etc.) and control of the display.

The control cabinet 30 may further include devices to measure, record and/or provide a report (e.g., hardcopy form or for display) of system conditions (e.g., time, date, temperature, etc.) as described below. For example, the control cabinet 30 may include a slot, preferably defined in top wall 187, to enable a hardcopy report to be retrieved from the system by a user. However, the slot may be defined at any location on the power supply cabinet. The report provides medical personnel documentation for their files on the heating characteristics of the solution. The information may include the start date and start time of solution or other item heating, the time interval the solution or other item was heated, the temperature the solution or other item attained during heating and/or the time and temperature of the solution or other item when the solution was removed from the system (e.g., partial or complete history of time and solution or other item temperature). The report may further include a variety of information (e.g., facility name and location, patient information, doctor information, type of procedure, type of solution, items being heated, amount or quantity of solution or other item being heated, etc.).

A suitable connecting member (not shown) may be provided on temperature control cabinet rear wall 183 to secure the control cabinet 30 to a support structure. For example, the connecting member may be a mounting clamp for securing cabinet 30 to an IV pole. The mounting clamp is configured to permit mounting of the control cabinet 30 in a variety of selected orientations with respect to the IV pole so as to permit the front portion of the control cabinet to face the user during system operation. Alternatively, the connecting member may include a wall mounting or any other suitable connector for securing the cabinet 30 directly to a wall or other surface.

A cable port is disposed on top wall 187 of the control cabinet housing 181 and is configured to receive another end of the connection cable or cord 180 that operatively connects control cabinet 30 to the heating cabinet 20 (as described above). The cable port may be configured to releasably or permanently secure the connection cord 180 to the temperature control cabinet 30. The side wall 185 of the housing 181 may further include a bracket 199 that provides a storage location for the connection cord 180 (e.g., when one or both ends of the cord are disengaged from the heating and/or power supply cabinets) and/or an outlet power cord for receiving power from a wall outlet (e.g., by wrapping the power supply cord around the bracket). Alternatively, the control cabinet 30 may include one or more retractable cord mechanisms that retract the connection cord 180 and/or the outlet cord into the temperature control cabinet 30 for easy storage.

As noted above, the system includes a fluid conduit that directs fluid from the solution container 60 downstream toward the patient. An inline heating assembly 40 is disposed at any suitable location along the fluid conduit. In the embodiment shown in FIG. 1A, the fluid conduit includes a first fluid conduit section 35A (e.g., an IV line) disposed upstream from and in fluid communication with the inline assembly 40, and a second fluid conduit section 35B (e.g., an IV line or a medical instrument such as a catheter) disposed downstream from and in fluid communication with the inline assembly. The first fluid conduit section 35A, in turn, is in fluid communication with the storage container 60 such that fluid within the container is permitted to flow through conduit.

Figure 2A:
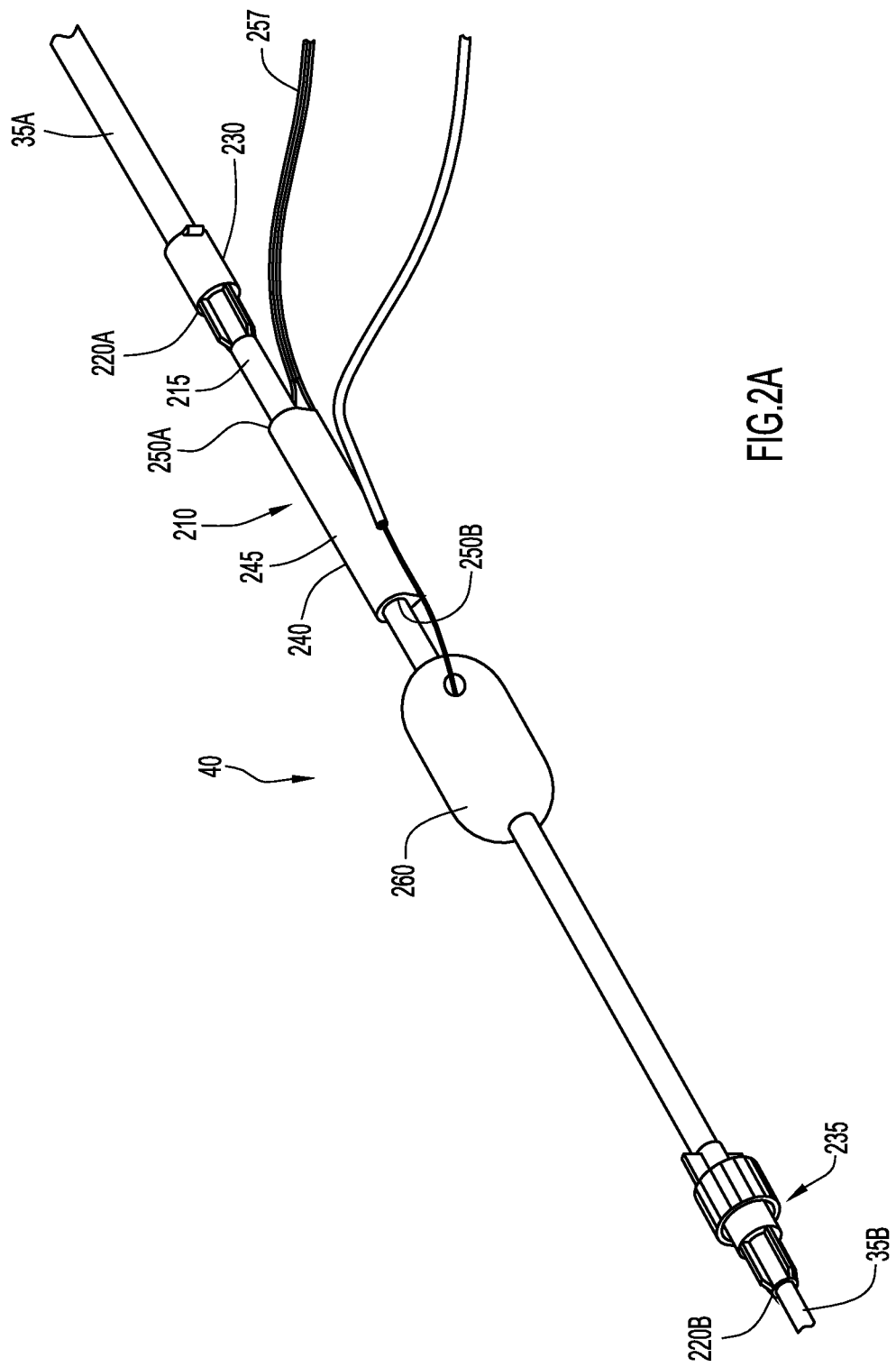
FIG. 2A illustrates a perspective view of the heater assembly in accordance with an embodiment of the invention.
Figure 2B:
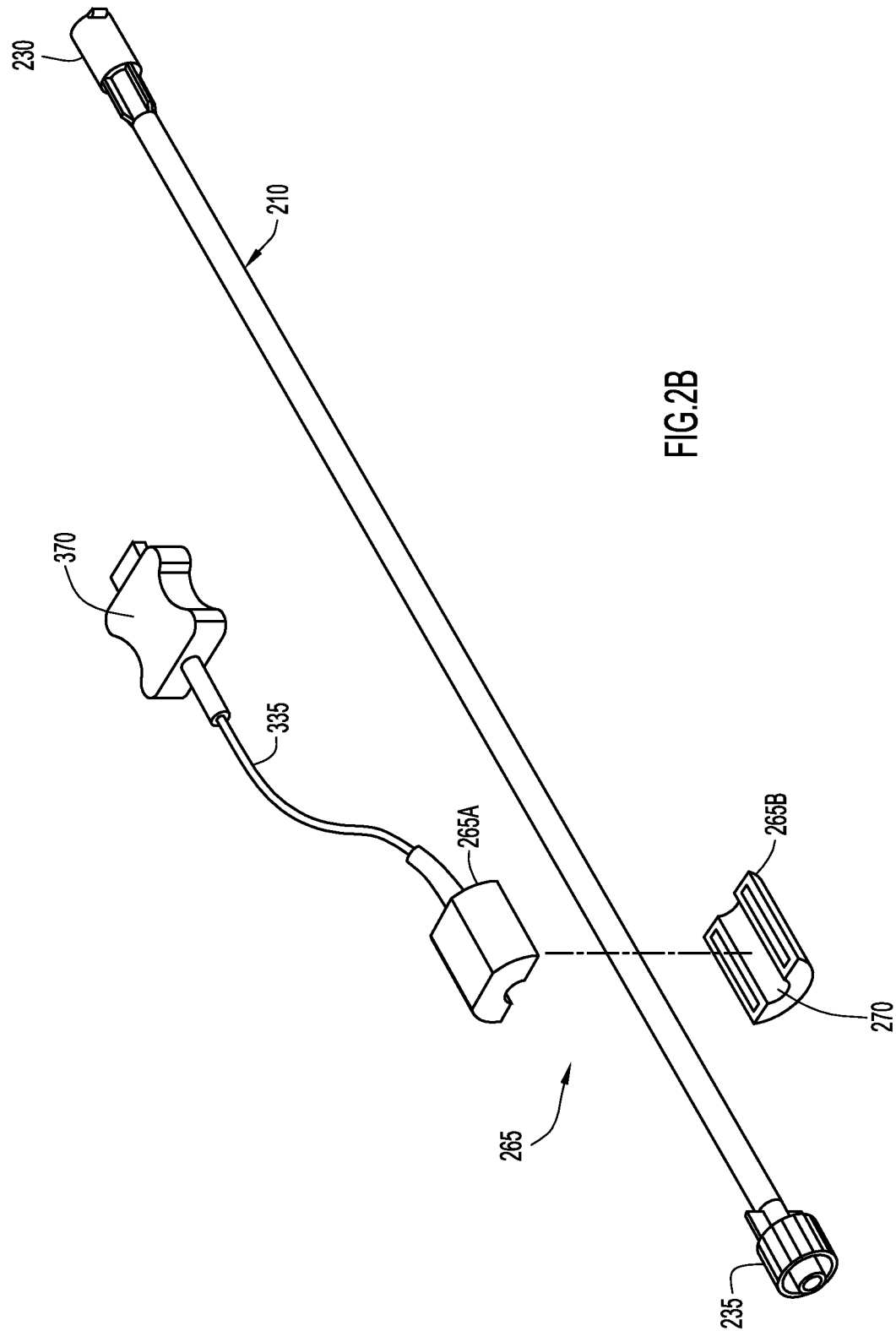
FIG. 2B illustrates an exploded view of the temperature sensor of the heater assembly shown in FIG. 2A.

Referring to FIGS. 2A and 2B, the inline assembly 40 includes elements that heat and/or monitor the temperature of the fluid passing from the conduit first section 35A to conduit second section 35B. The inline assembly 40 includes a fitting 210 defined by an elongate, substantially cylindrical base portion 215 having an internal channel extending from a first or upstream open end 220A to a second or downstream open end 220B. The proximal portion of the first conduit section 35A is attached to the storage container 60, while the distal portion of the first conduit section is attached to the upstream end 220A of the fitting 210. Similarly, the downstream end 220B of the fitting 210 is attached to the second conduit section 35B. With this configuration, the base portion 215 permits fluid flowing along the first conduit section 35A to pass through the fitting 210 and to the second conduit section 35B.

The open ends 220A, 220B of the fitting 210 may be releasably coupled to the conduit portions 35A, 35B. By way of example, fasteners such as Luer locks may secure the fitting to the conduit portions 35A, 35B. By way of specific example, the upstream end 220A of the fitting 210 may include a female Luer 230 and the downstream end 220B may include a male Luer 235. With this configuration, the fitting 210 is removable from the fluid conduit, making the inline assembly 40 disposable after each use to maintain fluid sterility. Alternatively, the fitting 210 may be permanently secured to the fluid conduit (e.g., by welding the ends of the fitting to the conduit portions 35A, 35B) to form, e.g., a disposable IV line set.

The fitting 210 may be constructed of plastic or any other rigid material suitable for use with fluid conduits such as IV lines. The fitting 210, moreover, may possess any shape and dimensions suitable for its described purpose. By way of example, the fitting 210 may possess a length of approximately 10 inches.

An inline heater 240 is disposed on the fitting 210 at a location intermediate the fitting open ends 220A, 220B. The inline heater 240 is configured to heat the solution as it passes through the fitting 210. In general, as solution passes through a fluid conduit such as an IV line, the fluid loses heat, creating a situation in which the temperature of the fluid measured at the solution container 60 differs from that of the fluid exiting the conduit. Consequently, heating the fluid as it travels through the fitting 210 maintains the fluid at a temperature most desired for a particular medical procedure.

The inline heater 240 may be in the form of a clip-on heater having a generally elongated, cylindrical body 245 within an internal channel or bore extending longitudinally therethrough. The surface of the interior channel may be contoured complimentary to the exterior surface of the fitting 210. The inline heater body 245 further includes a first open end 250A and a second open end 250B. The inline heater body 245 may include a slit or slot extending from the first body open end 250A to the second body open end 250B. The inline heater body 245 may be flexibly rigid, thereby permitting the faces of the slit to separate when appropriate force is applied, but returning to their normal, closed position when the force is removed. With this configuration, inline heater 240 mounts onto the fitting 210 such that the interior channel of the inline heater is in snug, continuous contact with the exterior surface of the fitting. In operation, the inline heater transfers heat to the fitting 210, which, in turn, heats the fluid traveling through the fitting. The inline heater 240 may be electrically coupled to the inline display device 55 via wiring 257. Alternatively, the inline heater 240 is electrically coupled directly to the control cabinet 30 via the heater wiring 257.

In another embodiment, the inline heater body 240 may possess a unitary/continuous structure (containing no slit) and/or may be permanently secured to the fitting 210. In still another embodiment, the inline heater 240, instead of coupling to the fitting 210, may be integrated into the fitting 210.

The inline heater 240 may be of any suitable shape and possess any suitable dimensions. By way of example, the inline heater 240 may be in the form of a hollow cylinder adapted to snugly engage the fitting 210. By way of specific example, the heater may possess a length of approximately 1 inch to approximately 2 inches. The inline heater assembly 40 may include any quantity of heaters 240 disposed at any suitable locations along the fitting 210. That is, while illustrated as a single unit, the inline heater 240 may include multiple units longitudinally spaced along the fitting 210. By way of example, a heater may be disposed proximate the upstream opening 220A of the fitting 210 and a heater may be disposed proximate the downstream opening 220B of the fitting. The plurality of spaced heaters may be engaged/operated collectively or individually (i.e., selectively operated to provide the desired amount of heating to the desired area of the fitting 210).

The inline assembly 40 may further include an inline temperature sensing device 260 operable to measure the temperature of the fluid traveling through the fitting 210. The temperature sensing device 260 is disposed at a location intermediate the fitting open ends 220A, 220B. By way of specific example, the temperature sensing device 260 may be located downstream from the inline heater 240 (e.g., spaced approximately two inches from the Luer 235 disposed on downstream end 220B of the fitting). In another embodiment, the temperature sensing device 260 may be located upstream from the inline heater 240. In still another embodiment, a temperature sensing device 260 may be located both upstream and downstream from the inline heater 240.

The temperature sensing device includes a body that houses one or more temperature probes configured to measure the temperature of fluid flowing within the fitting 210. Referring to FIG. 2B, the inline temperature sensing device 260 includes a body 265 having a first or upper body portion 265A and a second or lower body portion 265B. Each body portion 265A, 265B may be substantially U-shaped, including a curved medial portion and a pair of opposed arms. The body portions 265A, 265B may be secured together utilizing an adhesive (e.g., a cyanoacrylate adhesive). Once secured together, the body portions 265A, 265B cooperate to define a central bore 270 extending longitudinally through the body 265 from a first bore open end to a second bore open end. The interior surface of the central bore 270 is contoured such that it is complementary to that of the exterior surface of the fitting 210. With this configuration, the temperature sensing device 260 mounts onto the fitting 210, with the central bore 270 receiving the fitting 210 and the interior surface of the central bore 270 being in snug contact with the exterior surface of the fitting.

Figure 3A:
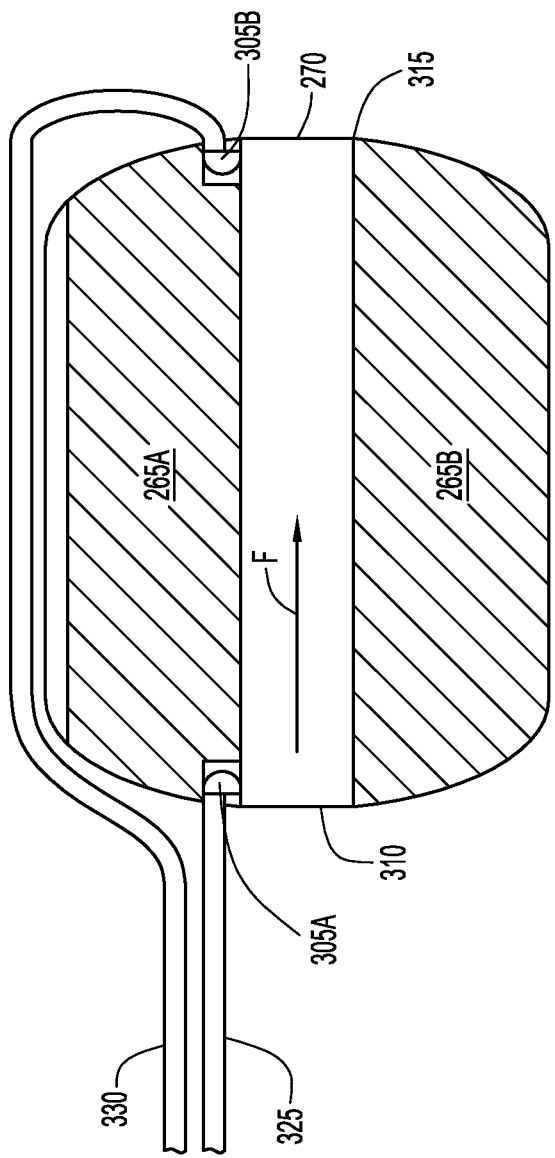
FIG. 3A illustrates a cross sectional view of the temperature sensor in accordance with an embodiment of the invention.

In one embodiment, the temperature sensing device 260 includes a temperature sensor configuration that measures the temperature of the fluid at two separate positions/points along the body 265. Referring to FIG. 3A, the first body portion 265A includes a first or inlet temperature sensor 305A and positioned at a first or upstream open body end 310 (also called an inlet) and a second or outlet temperature sensor 305B located proximate a second or downstream body end 315 (also called an outlet). The inlet sensor 305A may be operatively connected to the controller cabinet 30 via a first wire 325 while the outlet sensor 305B may be operatively connected to the controller 30 via a second wire 330. The wires 325, 330, in turn, are housed within inline cable 335 (seen in FIG. 2B). With this configuration, the inlet sensor 305A measures the temperature of the fluid (TO proximate the inlet 310 of the temperature sensing device 260, while the outlet temperature sensor 305B measures the temperature of the fluid (Te) proximate the outlet 315 of the temperature sensing device.

At constant flow rate and uniform conduit geometry, fluid heat loss rate is substantially constant as a function of travel time within the fluid conduit. Thus, the change in fluid temperature can be measured for a predetermined distance of travel using two measurement points. Thus, under Normal Operation (Tf>Te), as fluid travels the length of the body 265, it is expected to cool a certain amount based on the ambient temperature and the time spent in the body. This cooling can be detected by placing temperature sensors 305A, 305B at the inlet (Tf) and the outlet (Te). This change in temperature is proportional to flow rate (flow indicated by arrow F). Thus, the flow rate can then be approximated and used to control ramping profiles within the control cabinet 30 for the inline heater 240.

This information can also be utilized to identify an abnormal condition that necessitates termination of the inline heater 240. For example, information regarding fluid temperature can also be used to detect the presence of a heat source near the temperature sensing device 260. Thus, if Te>Tf or if Tf−Te falls out of a specified range, it is likely that an external heat source is present that prevents the fluid heat loss or that there is a sensor failure. In either case, the inline heater 240 could be shut down and an alarm sounded.

Figure 3B:
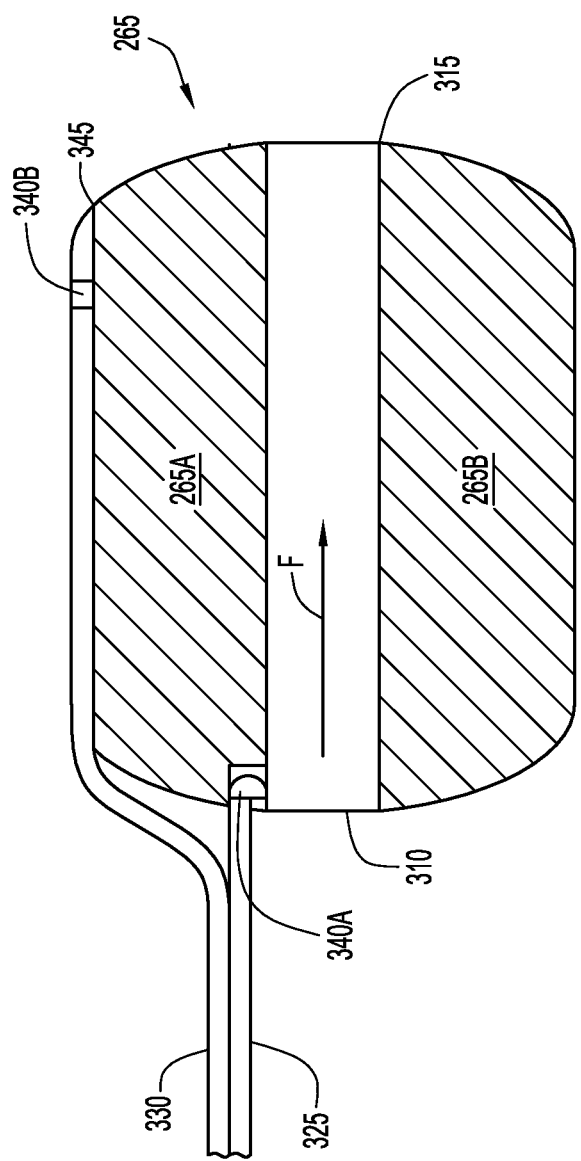
FIG. 3B illustrates a cross sectional view of the temperature sensor in accordance with another embodiment of the invention.

Referring to FIG. 3B, in another embodiment, the temperature sensing device 260 includes a temperature sensor configuration operable to measure the difference between the fluid temperature within the conduit and ambient temperature. Specifically, a first or inlet temperature sensor 340A is disposed within the body 265 (e.g., at the first body open end 310) proximate upstream end 310. In addition, a second or ambient temperature sensor 340B is disposed on an exterior surface 345 of the body 265 (e.g., along the exterior surface of the upper body portion 265A). The inlet sensor 340A is operatively connected to the control cabinet 30 via the first wire 325, and the ambient sensor 340B is operatively connected to the control cabinet 30 via the second wire 330. The wires 325, 330, in turn, are housed within inline cable 335 (FIG. 2B). With this configuration, the inlet sensor 340A measures the temperature of the fluid (Tf) proximate the inlet 310 of the temperature sensing device 260, while the ambient temperature sensor 340B measures the ambient temperature (e.g., the surface temperature or the air temperature adjacent the body 265).

Under normal operating conditions (Tf>Ta), for all expected operating temperatures, the temperature of the fluid (Tf) will be higher than ambient temperature (Ta). This, in turn, causes a temperature gradient to form, with heat dissipating from warm fluid to cold ambient. As a result, a range of gradients can be determined without placing measurement equipment directly within the fluid flow while accounting for the environment.

Abnormal operating conditions occur when the measured ambient temperature is equal to or greater than the measured inlet fluid temperature (Tf=/<Ta). Potential causes of this condition include the presence of a warm hand or electric blanket on top of the temperature sensing device 260. If this condition occurs, it is impossible to determine which temperature the inlet sensor 340A is measuring, or how temperature fluctuations in the ambient or fluid will affect the reading. Also, if Ta>Tf (ambient temperature higher than the fluid temperature), then fluid warming may be occurring that is not being measured by the inlet sensor 340A. This could lead to a fluid temperature runaway situation, which risks harm to the patient. Under these situations, the inline heater 240 would be shut down and an alarm may be activated to alert medical professions of the situation (e.g., an audible alarm).

The temperature sensors 305A, 305B, 340A, 340B may be implemented by any conventional or other type of temperature sensor (e.g., RTD, IR, NTC, thermistor, thermocouple, etc.) for measurement of fluid and/or ambient temperatures. Referring back to FIGS. 2A and 2B, the sensor wiring 325, 330, housed in cable 335, emerges from the upper body portion 265A and terminates in a plug 370. The plug 370, in turn, may electrically couple to the inline temperature display 55 via a mating portion disposed on the display. Alternatively, the plug 370 may electrically couple directly to the control cabinet via a mating port disposed at any suitable location on cabinet housing 181 adapted to receive the plug 370.

The inline display device 55 may be connected to the temperature sensing device 260 to communicate with the temperature sensing device, e.g., to display the fluid and/or ambient temperature measured by the sensors 305A, 305B, 340A, 340B. Referring to FIG. 4, the inline display device 55 includes a digital display 410 (e.g., LCD or LED) for displaying temperatures and other information. The sensor wiring 325, 330 (housed in cable 335) connects to the inline display 55 via plug 360, transmitting signals indicating temperature information measured by the temperature sensors 305A, 305B, 340A, 340B.

The inline display device 55, moreover, may be connected to the inline heating unit 240, communicating with the inline heating unit, e.g., to provide power to the inline heating unit. Specifically, wiring 257 from the inline heating unit 240 may connect to the inline display 55 via plug 420. The inline display 55 may further be electrically coupled to the control cabinet 30 via wiring 430.

Figure 5:
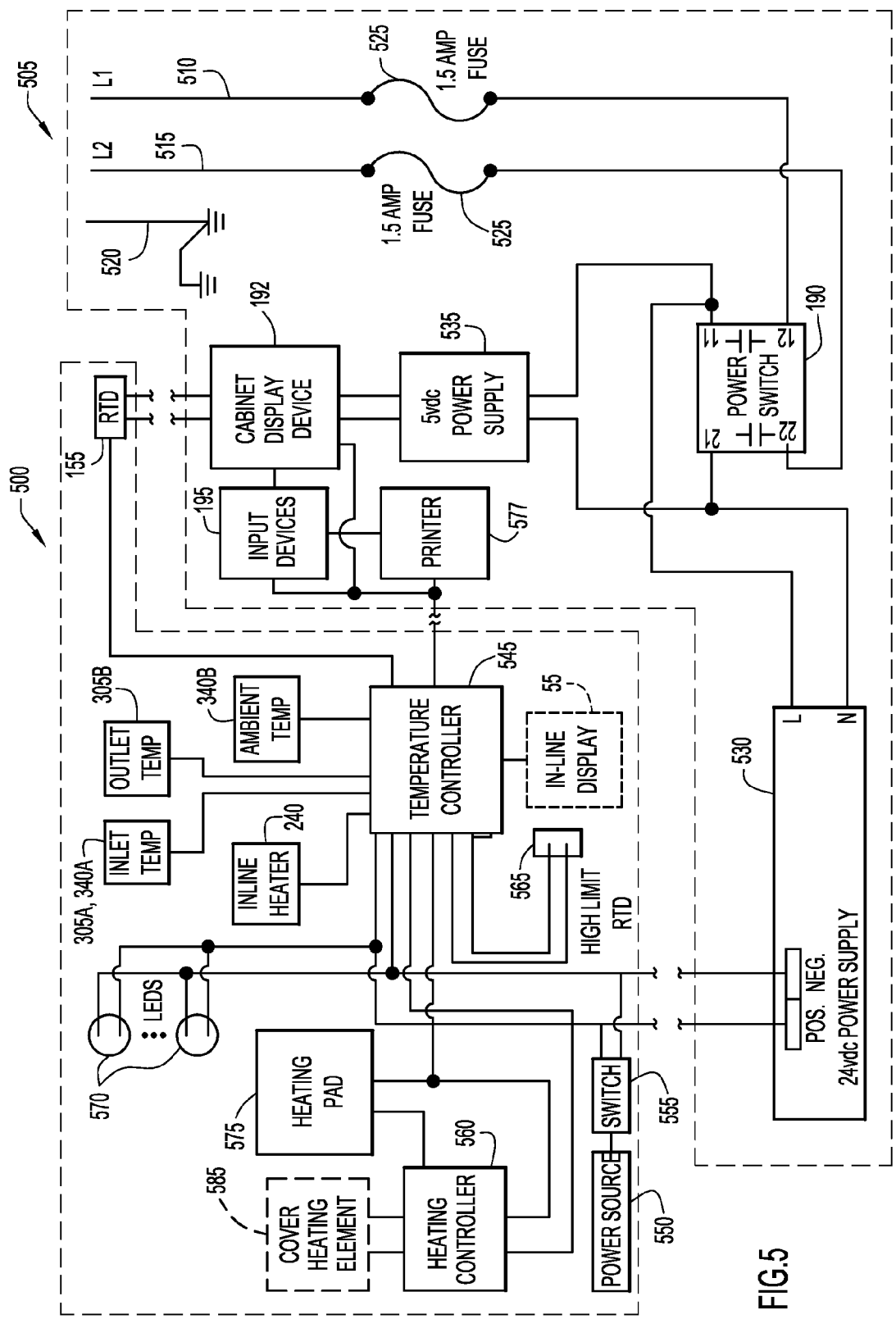
FIG. 5 illustrates an electrical schematic diagram of an exemplary control circuit for the system of FIG. 1A.

An exemplary control circuit for controlling system operation is illustrated in FIG. 5. The control circuit is divided into two dotted line sections to identify a heating control circuit 500 disposed in heating cabinet 20 and a power supply circuit 505 disposed in control cabinet 30, where the circuits are coupled as described below via power supply cord 180. Referring to power supply circuit 505, lines 510, 515, and 520 conduct power received from the outlet power cord (not shown) of control cabinet 30, where line 520 is connected to ground. Lines 510, 515 are each connected in series with a corresponding fuse 525, preferably a 1.5 amp fuse, to protect the circuit from power surges and spikes. Lines 510, 515 extend from fuses 525 to the power switch 190 (FIG. 1) that controls power to the circuit. The power switch 190 enables a main power supply 530 (e.g., a 24V dc power supply) to provide power to the heating cabinet 20 via power supply cord 180. The power switch 190 further enables a display power supply 535 (e.g., a 5V dc power supply) to provide power to a cabinet display device 192 in the control cabinet 30 or to the optional inline display 55. The display devices 55, 192 may receive information from a temperature controller 545 or may include a controller to process signals received directly from various sensors (e.g., temperature sensor 155, 305A, 305B, 340A, 340B) for displaying measured information.

With reference to heating control circuit 500, temperature controller 545 is connected to the power supply 530 in the control cabinet 30 via the power supply cord 180. Power may alternatively be supplied to the temperature controller 545 from a power source 550 (e.g., a battery) via switch 555 when the heating cabinet 20 is disconnected from the controller cabinet 30 (e.g., during transport). The temperature controller 545 is capable of measuring time to provide reports of solution temperature. The temperature controller 545 is connected to a heating controller 560, a high limit temperature sensor 565, the cabinet temperature sensor 155, a power indicator 570, and a heating pad 575. The temperature controller 545 is further connected to the inline heater 240 and the sensors of the temperature sensing device 260. Specifically, the temperature controller 545 is connected to the temperature sensing device including the inlet sensor 305A and the outlet sensor 305B, and/or to the temperature sensing device including the inlet sensor 340A and the ambient sensor 340B.

In addition, the temperature controller 545 may further be coupled to a printer 577, input devices 195 (FIG. 1), and the cabinet display device 192 (FIG. 1) within the power supply circuit 505 via cord 180. The power indicator 570 is also connected to power supply 530. The power indicator 570 preferably includes one or more LEDs disposed on the heating cabinet housing (as described above) to provide an indication that the heating cabinet 20 is receiving power from the control cabinet 30 and is operating to maintain the container 60 at the desired temperature.

The temperature sensor 155 of the heating cabinet 20, which extends through heating plate 110, may be connected to display device 192 disposed in the power supply cabinet via power supply cord 180. The cabinet temperature sensor 155 provides signals to display device 192 for displaying measured temperature information of the solution container 60. Alternatively, the display device 192 may receive the temperature information from the temperature controller 545.

Each of the inline heater 240, inlet temperature sensor 305A, 340A, outlet temperature sensor 305B, and the ambient temperature sensor 340B may be connected to the temperature controller 545 via wires 325, 330 contained in cord 335 that connects to control cabinet 30.

Heating controller 560 is connected to the heating pad 575 (which heats heating plate 110), to the inline heater 240, and to a heating element 585 contained in the cover 115 (when the heating element is employed). The heating controller 560 is typically set to provide power to one or more of the heating pad 575, the inline heater 240, and heating element 585 to maintain each component at the same or different predetermined temperatures (e.g., the heating controller may maintain all devices at about 43° C.). Optionally, the heating controller 560 may further be connected with the cabinet temperature sensor 155 to control the supply of power to the heating pad 575 and the cover heating element 585 based upon temperature measurements of the solution container 60 by the cabinet temperature sensor 155. In addition, the heating controller may further be connected with the temperature sensors 305A, 305B, 340A, 340B of the temperature sensing device 260 to control the supply of power to the inline heater 240 upon temperature measurements of the fluid traveling through the fitting 210.

The temperature controller 545 controls power to the heating controller 560 based on a temperature measurement of the heating pad 575 via a high limit temperature sensor 565. In addition, the temperature controller may apply heater controls based on heat ramps/profiles (e.g., via look-up tables with predetermined control parameters based on time and temperature). The high limit temperature sensor 565, preferably a resistive temperature device (RTD), measures resistance through the heating plate 110 and provides a temperature indication to the temperature controller 545. The temperature controller 545 disables power to heating controller 560 in response to the measured temperature by the high limit temperature sensor 565 that exceeds a predetermined excessive threshold temperature for the heating plate 110 (e.g., a measured heating plate temperature exceeding 44° C. or other desired threshold temperature). In effect, this arrangement serves as a shut-off safety device to disable the heating plate 110 and heating element 585 in response to excessive heating plate temperatures. The heating element 585 and heating plate 110 may alternatively be controlled by respective individual controllers based on measured temperature values of the solution container 60 or other items (e.g., heating plate, heating element, heating pad, etc.).

Similarly, the temperature controller 545 controls power to the inline heater 240 based on a temperature measurement of the sensors 305A, 305B, 340A, 340B via the high limit temperature sensor 565. The high limit temperature sensor 565 measures resistance through the inline heater 240 and provides a temperature indication to the temperature controller 545. The temperature controller 545 disables power to heating controller 560 in response to the measured temperature by the high limit temperature sensor 565 that exceeds a predetermined excessive threshold temperature for the inline heater 240.

Alternatively, the heating controller 560 may be set to maintain the solution container 60 at a desired temperature that is entered by the user via input devices 195 disposed on the control cabinet 30 near display device 192. Desired temperature information may be sent from the input devices to heating controller 560 via a circuit connection extending through the power supply cord 180 to link these two components. The input devices 195 may be connected to display device 192 to facilitate display of time, temperature, or other information entered by the user. The input devices 195 may further be connected to printer 577 to facilitate the printing of information processed by the control circuit. The heating controller 560 may be configured to control power supplied to the heating pad 575 and the heating element 585 based upon a comparison of the measured solution container temperature (e.g., provided to the heating controller by cabinet temperature sensor 155 via a connection within the heating control circuit 500) and the desired temperature. When the measured solution container temperature is below the desired temperature, the heating controller 560 maintains or enables power to heating pad 575 and heating element 585. Conversely, if the measured solution container temperature exceeds the desired temperature, the heating controller 560 disables power to the heating pad 575 and heating element 585. Thus, the heating controller 560 may maintain the solution container 60 at a desired temperature entered by the user by enabling or disabling power to the heating pad 575 and heating element 585.

Input devices 195 on the control cabinet 30 may further facilitate entry of an excessive threshold temperature for the heating plate 110 to control when the temperature controller 545 enables or disables power to the heating controller 560. Specifically, the temperature controller 545 may be connected to input devices 195 disposed on the control cabinet 30 to facilitate a comparison of the heating pad temperature measured by high limit temperature sensor 565 and the excessive threshold temperature for the heating plate 110 entered by the user in order to determine whether to shut off power to the heating controller 560. It is further noted that input devices may be disposed directly on the heating cabinet 20 to facilitate the entry of desired temperature information to the heating controller 560 and/or temperature controller 545.

The heating controller 560 may control any quantity of heating pads 575, heating elements 585, and/or inline heating devices 240. Alternatively, the heating control circuit 500 may employ a heating controller 560 for each heating pad 575 disposed on the heating plate 110 and/or heating element 585 (to control the solution bag temperature), as well as for each inline heater 240.

The temperature controller 545 may be implemented by any conventional or other controller or microprocessor (e.g., chip, card, processor, circuitry, etc.) and receives various information (e.g., enablement of heating cabinet temperature, etc.) related to thermal treatment of the solution. The temperature controller 545 may receive any additional information (e.g., facility information, doctor information, patient information, item (e.g., solution, instrument, etc.) information, etc.) from medical personnel or users via input devices 195.

The temperature controller 545 may further be configured to track/maintain parameters such as the date, elapsed heating time and occurrence time of an event or condition (e.g., the time when medical solutions are inserted and/or removed from the system, etc.). The temperature controller 545 may measure the elapsed time or record an occurrence time based on signals received from the heating 20 and/or control 30 cabinets, temperature sensors 155, 305A, 305B, 340A, 340B and/or input devices 195. For example, the temperature controller 545 may initiate measurement of a time interval in response to enablement of the heating or control cabinet, and may store the elapsed and/or occurrence time in response to any condition (e.g., when solution or other item is removed). The temperature controller 545 may further measure elapsed time or record elapsed and/or occurrence time in response to medical personnel manually entering information on input devices 195 (e.g., start and stop keys).

The temperature controller 545 may be configured to collect the appropriate information and to arrange the information into a report. The report may be arranged in any fashion and include any desired information. Moreover, the report and/or information may be stored in a memory device (e.g., local controller memory, removable memory, card, disk, etc.) for later retrieval as described below. In addition, the temperature controller 545 is coupled to display 192 to display the elapsed (or running) time, report or any desired information to medical personnel. The information displayed may be selected via input devices 195. The report may further be printed via printer 577. The printer 577 and display 195 may be implemented by any conventional or other printer and/or display devices.

The temperature controller memory is used to store the collected information. Basically, the temperature controller logs records containing system information (e.g., the date/time that medical solution is inserted into heating cabinet 20, the date/time that the medical solution is removed from the system, temperatures, etc.). In this manner, use of the system is documented with recorded log entries. Log triggering events can be user defined via input devices 195 that allow the system to be configured to record information in response to a wide variety of detected conditions, continuously, and/or at particular times or periodic intervals. The memory can be used to store a wide variety of information related to use of the system and the memory may alternatively be implemented by an electronic memory chip, a smart card, a floppy disk, a fixed or removable magnetic disk. The temperature controller may be configured to support one or more of those memory storage types.

The information collected and/or recorded by the temperature controller 545 and produced in a report can include, but is not limited to: the date/time that a medical solution was placed into/removed from the heating cabinet, the temperature of the medical solution upon being placed into/removed from the heating cabinet 20, the temperature of the medical solution at specific points in time while stored in the heating cabinet, start date and time that the medical solution began to be heated, the length of time that the medical solution was heated, the temperature that the medical solution was heated to during the heating cycle and/or the amount of solution or other item residing, placed in or removed from the system. The report may also include related information, such as patient information (e.g., name and identification number), facility information (e.g., name and location), doctor information, the type of procedure, the type of solution or other item being heated, the amount or quantity of fluid or other item being heated (e.g., fluid (or other item) level, volume or weight), the flow rate of fluid that is being heated, the temperature of fluid within the container or fluid line as the fluid is being infused, the pressure of fluid flow as the fluid is heated and any other desired information.

The system may employ any type of sensors or sensing devices (e.g., temperature sensors, presence sensors, weight sensors, volume sensors, pressure sensors, flow sensors, fluid sensors, fluid level sensors, etc.) to measure and provide any desired information to the temperature controller 545 for inclusion in a report. The recordation or collection may occur automatically or via user entered information (e.g., start, stop and/or record keys) as described above.

The temperature controller 545 stores and retrieves information from memory in order to produce a report. The report may be transmitted to printer 577 that is disposed within the control cabinet 30. The report may further be displayed by cabinet display device 192. The printer 577 basically provides a report in hardcopy form. The temperature controller 545 may control the printer to produce the report at specified times (e.g., termination of heating, at particular times of day, after a particular quantity of uses, etc.) or in response to requests from medical personnel via input devices 195 (e.g., print key). The printer 577 may print the report on any desired hardcopy medium. The printer 577 may place the information onto a label that is attached to a medical file. The information may be printed during or after the solution heating, or be stored on a memory device and printed at a desired time as described above. The printer 577 may further provide additional copies of the report in response to user requests, or a medium automatically creating duplicates may be utilized (e.g., carbon-less paper, etc.).

The report may alternatively be provided in electronic form. The temperature controller 545 may facilitate communication with other devices for transference or downloading of the report to those devices. For example, the information may be downloaded or transmitted over a network or other communications medium to another device (e.g., PDA, computer, another warming system, etc.) for viewing, storage and/or printing.

Information is collected by temperature controller 545 and stored in memory, typically in real-time, as events occur. Reports can be generated and printed/displayed in a timely manner to allow a local or remote (e.g., at a network workstation or computer) user to monitor the status of one or more systems and the status of medical solution undergoing thermal treatment. Alternatively, reports can be generated and printed/displayed at a time of a user choosing. For example, a user either local to or remote from a system is able to monitor the temperature of medical solutions and the time that medical solutions have been stored within a system based upon reports printed or shown on a display device. The user may access stored information relating to one or more systems by requesting (e.g., via temperature controller input devices, a remote workstation, etc.) that a report be produced or displayed to a specific printer or display (e.g., local or remote).

Figure 6A:
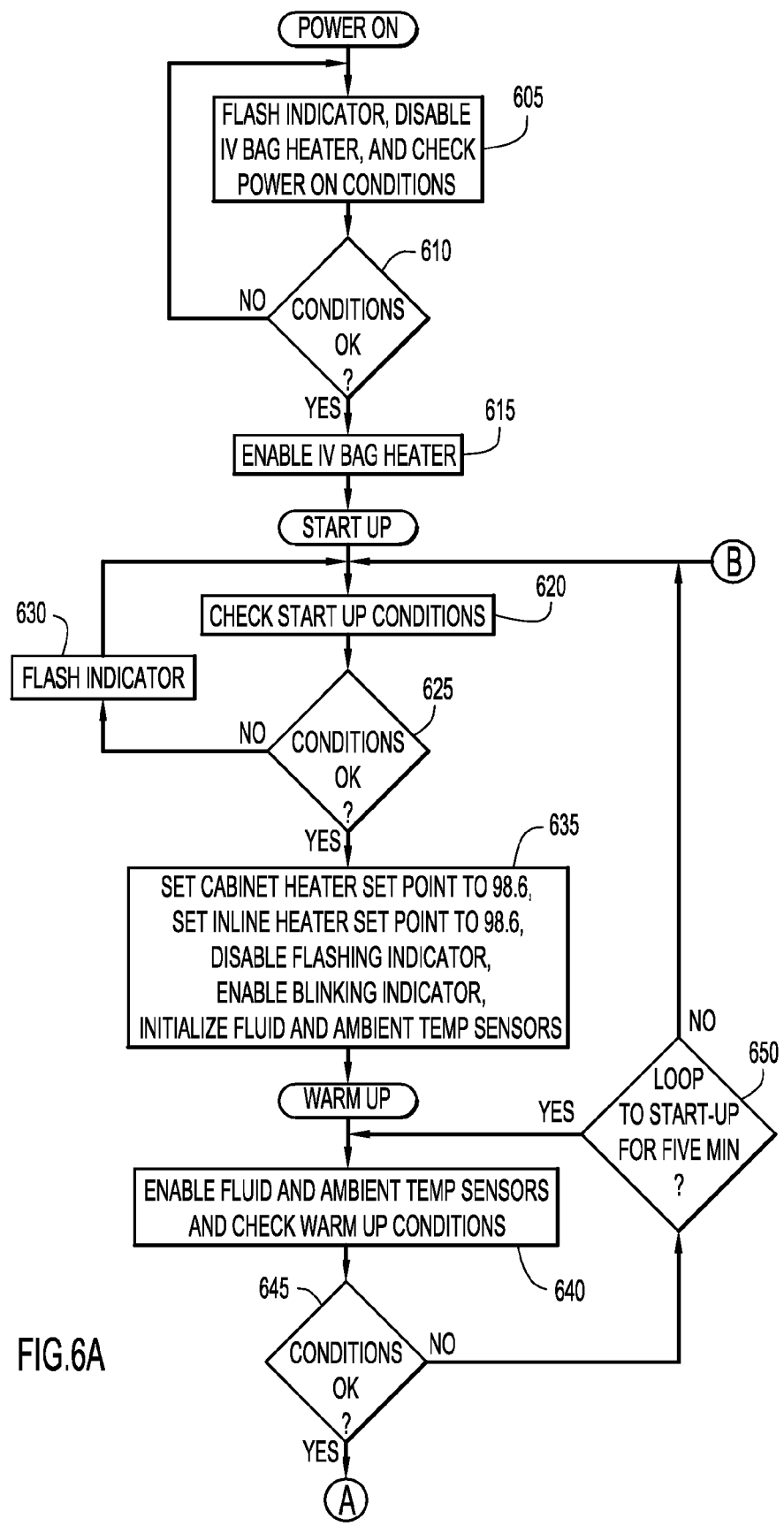
FIGS. 6A and 6B are flow charts showing the operational logic of the system in accordance with an embodiment of the invention.
Figure 6B:
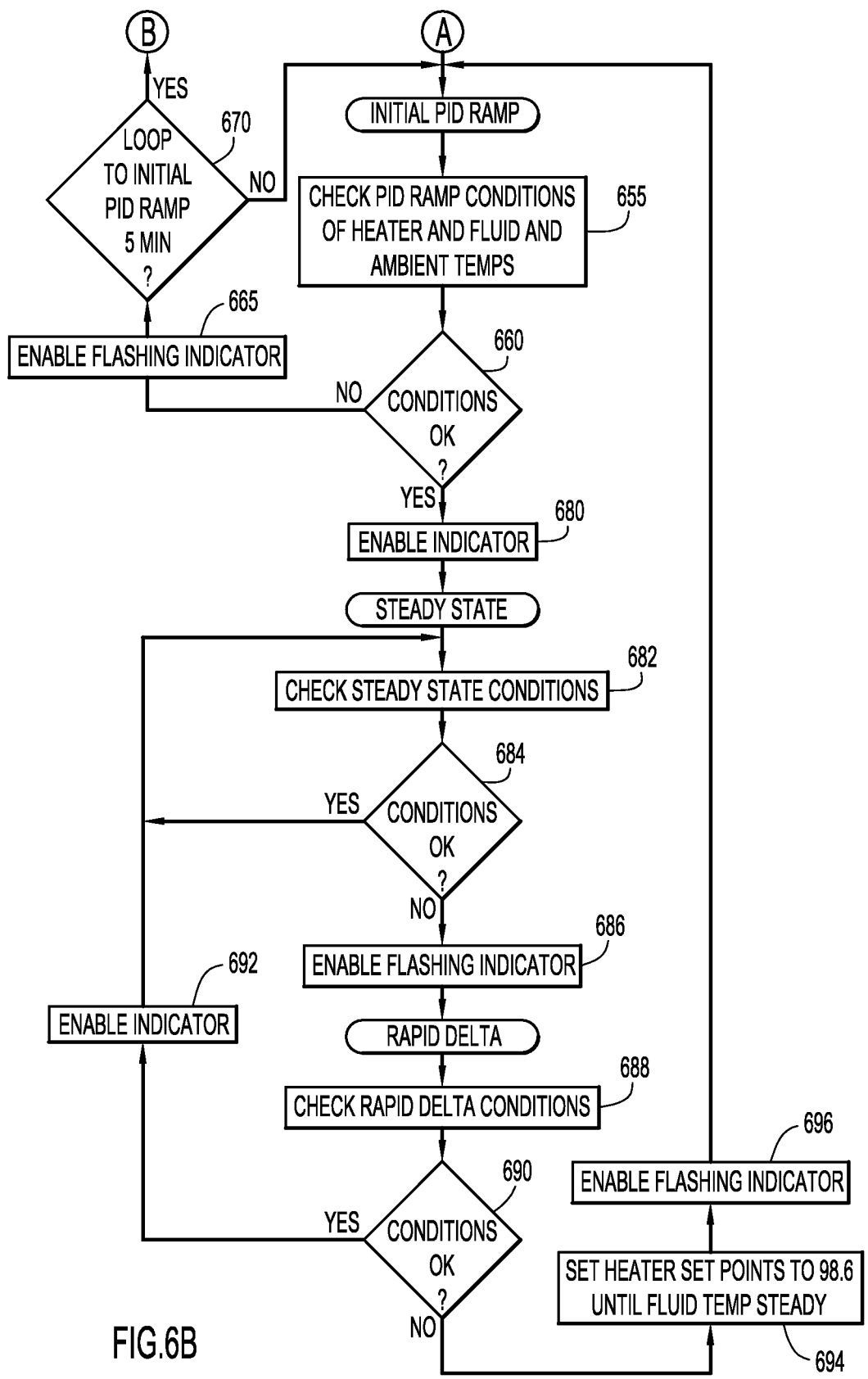

FIGS. 6A and 6B illustrate the operational flow chart of the system. During power up, at Step 605 the system initiates a flash indicator, disables heating components (the heating plate and/or heating element) of the heater cabinet 20, and checks "power on" conditions at Step 610 (e.g., the system may check whether the temperature sensors 305A, 305B, 340A, and/or 340B are connected and/or whether the sensors are operating within predetermined parameters). If the conditions are not acceptable, the system re-initiates the power on step.

If the conditions are OK, the system enables operation of the heating components in the heating cabinet 20 at Step 615 (thereby enabling heating of the solution container 60 and/or the inline heater 240). In addition, the system begins the start up procedure at Step 620, initiating a further flash indicator and checking start-up conditions (e.g., checking the connection of the sensors, the heating plate and/or the heating element), and further determining whether that the heating components and sensors are operating within acceptable parameters at Step 625. If any of the circuits are opened (indicating a disconnect of the sensors or heaters), or if any of the parameters are not acceptable, an alert is indicated at Step 630 (e.g., a flash indicator) and the start-up process is reinitiated. If parameters are acceptable, then the system may further set the heating components to a default temperature at Step 635. For example, the cabinet heaters 110, 585 are set to 98.6° F. and the inline heater 240 is set to 98.6° F. Additionally, the flashing indicator is disabled, the blinking indicator is enabled, and the sensors of the inline sensing device (i.e., the inlet 305A and outlet 305B fluid sensors and/or the fluid 340A and ambient 340B sensors) are initialized, being placed in standby mode.

After start-up, the warm-up process begins at Step 640, where the fluid and/or ambient temperature sensors 305A, 305B, 340A, 340B are enabled, a flashing indicator is engaged to indicate the warm up process has initiated, and the warm-up conditions are checked. For example, the system, at Step 645, confirms that the sensors and the heaters are operating within acceptable ranges and whether or not the set point temperature has been reached. If the parameters do not fall within desired ranges, at Step 650 the system activates an alert and either begins the warm-up process again or reinitiates the start-up process.

If the parameters fall within acceptable ranges (i.e., if warm-up conditions are OK), the initial PID ramp begins at Step 655 (FIG. 6B), during which the PID ramps conditions of the cabinet temperature sensor 155, as well as the fluid and ambient temperature sensors 305A, 305B, 340A, 340B are checked. The temperatures measured by the fluid and ambient temperature sensors are obtained, and the PID ramp profile is calculated. The system further checks whether or not the PID ramp falls within the ramp profile. If conditions do not fall within acceptable parameters, then, at Step 660, an alarm is initiated at Step 665 (e.g., a flashing indicator is enabled) and the system reinitiates the initial PID ramp at Step 670, or the start-up sequence is reinitiated (Step 620).

If the PID ramp conditions fall within acceptable parameters, then the indicator is enabled at Step 680 and the system enters steady state. At Step 682, the steady state conditions are checked. For example, the system confirms the heating components (the inline and cabinet heaters) and the sensors (the ambient and or fluid sensors) are operating within acceptable parameters. The system further confirms that a small temperature delta (e.g., less than five degrees Fahrenheit) exists for the heating components and the sensors, and/or whether the temperature difference between the fluid and ambient temperature sensor falls within the accepted value. At Step 684, if the conditions fall within acceptable parameters, then, the steady state is maintained.

If the conditions do not fall within acceptable parameters, however, an alarm is activated (e.g., a flashing indicator is enabled) at Step 686, and the rapid delta conditions are checked at Step 688. For example, the system checks whether the heating components and the sensors are operating within accepted parameters, whether the fluid temperature sensor is within a desired range, and/or whether the temperature difference between the fluid and ambient temperature sensor is within a predetermined amount. If the conditions fall within acceptable parameters, at Step 690 the "acceptable parameters" indicator is enabled at Step 692 and the system returns to steady state. If, however, the rapid delta conditions do not fall within acceptable parameters, then at step 694, the set points of the heating components are restored to 98.6° F., and are maintained until the measured fluid temperature is steady (i.e., the temperature measured by the fluid temperature sensor is steady). Then, at Step 696, an alarm is activated (e.g., by enabling a flashing indicator). The system then reinitiates the initial PID ramp (Step 670) or reinitiates the start-up sequence (Step 620).

Operation of the temperature controlled infusion system is described with reference to FIGS. 1-6B. Specifically, each of the heating 20 and control cabinets 30 are secured to a pole or other support structure in the manner described above, and a solution container 60 (e.g., an IV bag) is placed within heating plate 110 and secured therein by cover 115 and hook member 160. Power supply cord 180 is engaged at the power supply ports of each cabinet 20, 30 to facilitate a supply of power from the control cabinet 30 to the heating cabinet 20. Additionally, the wiring 257, 335 of the inline heater 240 and the inline sensor device 260, respectively, is connected to the inline display 55, which, in turn, is engaged to an inline port of the control cabinet 30. Alternatively, the wiring 257, 335 is engaged directly to the control cabinet 30 via one or more inline ports.

The power switch 190 on control cabinet 30 is enabled to provide power to system 10, which, in turn, activates power indicator 570 on heating cabinet 20 (i.e., the power indicator LEDs turn on) to indicate a power supply and activation of the heating cabinet. When cover 115 includes a bladder, the bladder may be inflated to provide a desired fluid flow rate as described above. The heating controller 560 is typically set to provide power to heating pad 575 (and to cover heating element 585, when that heating element is employed) in order to maintain the solution container 60 at a predetermined temperature as described above. The heating pad may be disposed on one or more of the heating plate panels 110. For example, the heating pad may be disposed on the heating plate middle panel, while heating plate side panels each conduct heat from the middle panel to evenly heat the solution container. Additionally, heating pads may be disposed on the side panels.

The temperature controller 545 monitors the temperature of heating plate 110 via high limit sensor 565 and shuts power off to the heating controller in response to the heating plate temperature attaining excessive levels as described above. Alternatively, temperature information may be entered by the user as described above to control operation of the heating controller and/or temperature controller. Thus, the heating and temperature controllers control power to the heating pad (and heating element) to ensure the solution container 60 is maintained at the desired temperature prior to and during dispensing of solution from the bag to a patient.

The temperature sensor 155 directly measures the solution container temperature and may provide the measured information to the temperature controller 545 and/or cabinet display device 192 to display the solution container temperature. In addition, orientation of the heating cabinet 20 with respect to the IV pole may be easily adjusted by the user by rotating the heating cabinet in a selected direction and to a selected degree about the securing pin of the support member to permit easy viewing of the front portion of the heating cabinet.

The heating cabinet 20 may further include secondary power source 550, as noted above, for situations in which the heating cabinet must be disconnected from the power supply cabinet during system operation. The secondary power source 550 preferably includes a battery and may be automatically and/or manually engaged or disengaged via the user-operable switch 555 in accordance with connection of the power supply cord 180 to the heating cabinet 20. Thus, the secondary power supply source 550 renders the heating cabinet 20 operable to maintain the solution container at the desired temperature when the heating cabinet is disconnected from the power supply cabinet.

The temperature controller 545 further monitors the temperature of the inline heating device 240 via high limit sensor 565 and shuts power off to the heating controller 560 in response to the inline heating device temperature attaining excessive levels as described above. Alternatively, temperature information may be entered by the user as described above to control operation of the heating controller 560 and/or temperature controller 545. Thus, the heating 560 and temperature 545 controllers control power to the inline heating device 240 to ensure the fluid traveling along conduit 35 is maintained at the desired temperature during flow to a patient. The inline sensing device 260 indirectly measures the temperature of fluid traveling through fitting 210 at inlet and outlet points of the device. Alternatively, the inline sensing device 260 indirectly measures the temperature of the fluid traveling through the fitting 210 and directly measures ambient temperature. The inline sensing device 260 may provide the measured information to the temperature controller 545, the cabinet display device 192, and/or the inline display device 55 to display the measured inline temperature.

Figure 7:
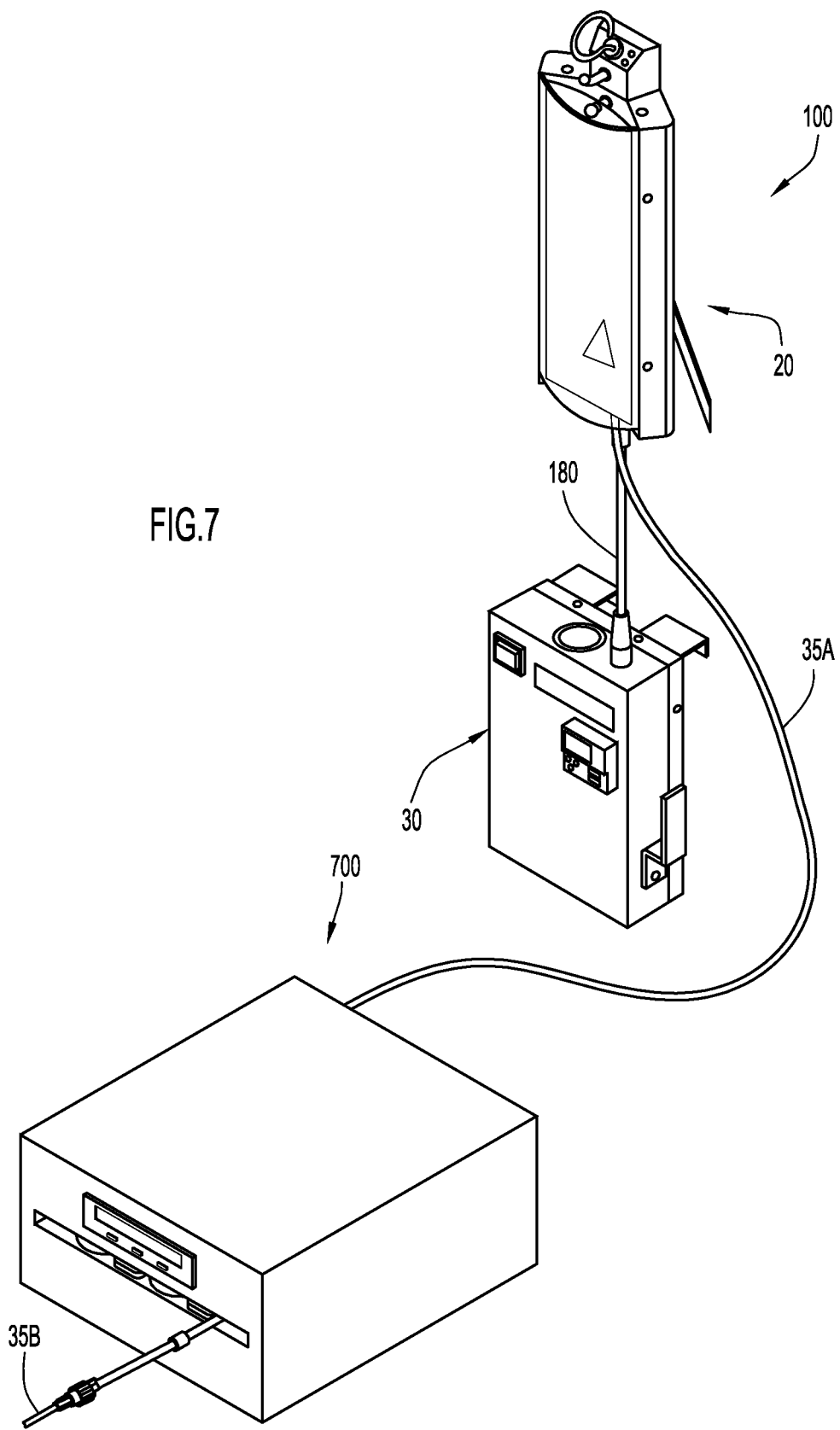
FIG. 7 illustrates a perspective view of a temperature controlled infusion system according to an alternative embodiment of the present invention

A temperature controlled infusion system 100 employing a warming unit 700 according to an embodiment of the present invention is illustrated, by way of example, in FIG. 7. Specifically, temperature controlled infusion system 100 is substantially similar to temperature controlled infusion system 10, and includes heating cabinet 20, temperature or power control cabinet 30, and a fluid conduit, each substantially similar to the corresponding components described above. Temperature controlled infusion system 100 further includes a warming unit 700. The fluid conduit is defined by first fluid conduit section 35A (e.g., an IV line) disposed upstream from and in fluid communication with warming unit 700, and a second fluid conduit section 35B (e.g., an IV line or a medical instrument such as a catheter) disposed downstream from and in fluid communication with the warming unit. The warming unit may include a warming device 1000, 1100 (FIGS. 10 and 11), and a cartridge 800 (FIG. 8) for insertion within the warming device to thermally treat infused fluids as described below. The heating cabinet 20 and/or temperature control cabinet 30 may be secured to any suitable support structure such as an IV pole, an operating table, a wall surface, a combination thereof, etc.

Figure 8:
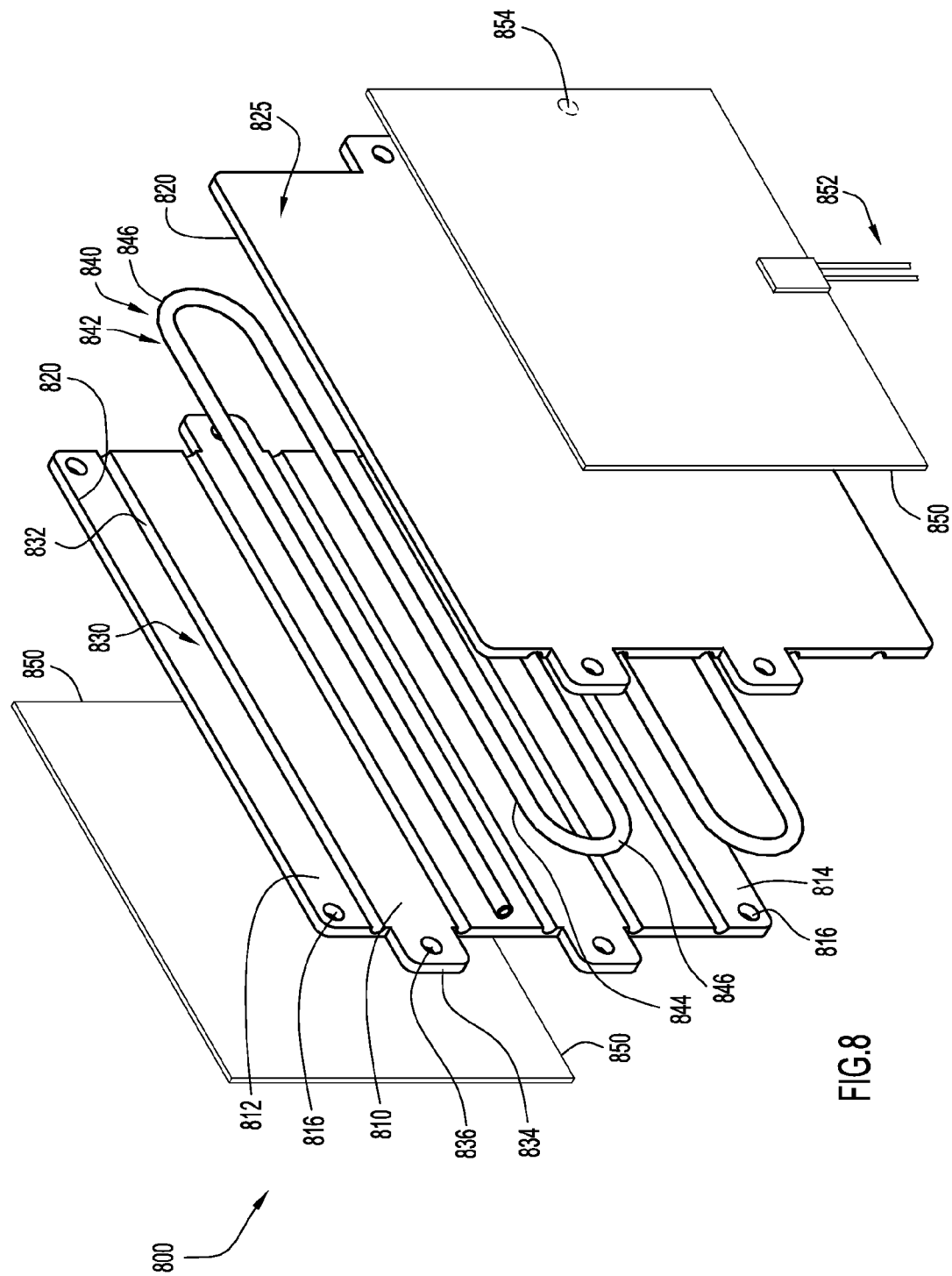
FIG. 8 is an exploded view in perspective of a warming device cartridge according to an embodiment of the present invention.

Cartridge 800 is illustrated, by way of example, in FIG. 8. In particular, cartridge 800 includes a plurality of heating plates 820, and a removable conduit 840 placed between the heating plates. Each heating plate 820 is preferably constructed of a suitably thermally conductive material (e.g., aluminum, etc.), and is substantially rectangular. The heating plates each include a generally smooth or planar exterior surface 825 and an interior surface 830. The exterior surface is in thermal communication with a corresponding heating element or pad 850 of a warming device to thermally treat fluid. The heating pad is preferably a polyimide heater pad, but may be implemented by any quantity of any type of conventional or other heating elements (e.g., pads, coils, strips, etc.).

Interior surface 830 includes a plurality of grooves or channels 832 extending substantially parallel to each other in a transverse direction relative to the heating plate (e.g., as viewed in FIG. 8). The grooves are spaced apart to basically partition interior surface 830 into a plurality of adjacent, substantially rectangular sections including upper and lower terminal sections 812, 814 and intermediate sections 810. Upper terminal section 812 is disposed at an upper portion of the interior surface (e.g., as viewed in FIG. 8) above the uppermost groove 832, while lower terminal section 814 is disposed at the lower portion of the interior surface below the lowermost groove 832 (e.g., as viewed in FIG. 8). Upper and lower terminal sections 812, 814 each include an aperture 816 defined therein toward each side edge. Intermediate sections 810 are disposed between the upper and lower terminal sections, and defined by adjacent grooves 832. The intermediate sections further include a projection 834 with an aperture 836 defined therein. Projections 834 extend transversely from opposing side edges of adjacent intermediate sections in an alternating fashion. The heating plates include substantially similar configurations, where grooves 832 of each heating plate combine to produce conduit channels to receive removable conduit 840 in response to placing the heating plates proximate each other in facing relation.

Conduit 840 includes an elongated tubular member 842 with a serpentine configuration, and is preferably constructed of a thermally conductive material (e.g., stainless steel, etc.)

in order to thermally treat fluid flowing therein. The serpentine configuration of tubular member 842 includes a plurality of substantially parallel linear sections 844 extending transversely relative to heating plates 820 (e.g., as viewed in FIG. 8) and connected via hair-pin curved sections 846. The length dimensions of linear sections 844 are substantially the same as grooves 832, while curved sections 846 extend beyond the confines of the grooves and reside external of the cartridge adjacent projections 834. The dimensions of the tubular member are less than the combined dimensions of groves 832 of the heating plates to enable reception of linear sections 844 of conduit 840 within the conduit channels formed by grooves 832 of the heating plates. The ends of conduit 840 are coupled to first and section fluid conduit sections 35A, 35B (FIG. 7) to enable the conduit to receive and thermally treat fluid from infusion system 100, and provide the thermally treated fluid to a patient. The conduit is removable from cartridge 800, and may be sterilized prior to each use via any suitable sterilization techniques (e.g., Autoclave, ETO, Gamma radiation, etc.). By way of example, the conduit includes a length of twenty inches, but may be of any suitable length or shape, and may be arranged in any desired configuration (e.g., linear, serpentine, circular, spiral, etc.).

Cartridge 800 is typically inserted within a warming unit employing heating pads 850 that apply heat to the exterior surfaces of heating plates 820. The heating pads include terminals 852 that provide power, control and/or other signals to control operation of the heating pads. In addition, a high limit temperature sensor 854 may be mounted on or proximate each heating pad to measure heating pad temperature and facilitate disablement of the heating pads in response to excessive temperatures. This prevents injury to patients based on receiving medical fluids at inappropriate temperatures.

Cartridge 800 may include various configurations to enable conduit 840 to be removed and inserted within the cartridge. Referring to FIG. 9A, cartridge 800 may, by way of example, include upper and lower heating plates 820 arranged with their interior surfaces in facing relation. In this case, grooves 832 of each heating plate combine to form the conduit channels to receive conduit 840, while apertures 816 and 836 of the heating plates are substantially aligned. A removable fastener 860 may be inserted through aligned apertures 816, 836 to removably fasten the heating plates together and secure conduit 840 therein. The fasteners may include any quantity of any type of fastener or securing device (e.g., bolt, screw, etc.). The fasteners may be manipulated (e.g., and withdrawn from the apertures) to enable separation of the heating plates, thereby transitioning the cartridge to an open state and enabling insertion and removal of conduit 840 from grooves 832 of the lower heating plate. Moreover, the fasteners may be (e.g., inserted and) manipulated within the apertures to enable the heating plates to be fastened together, thereby transitioning the cartridge to a closed state and securing conduit 840 within the conduit channels formed by the combination of grooves 832 from each heating plate.

Figure 9B:
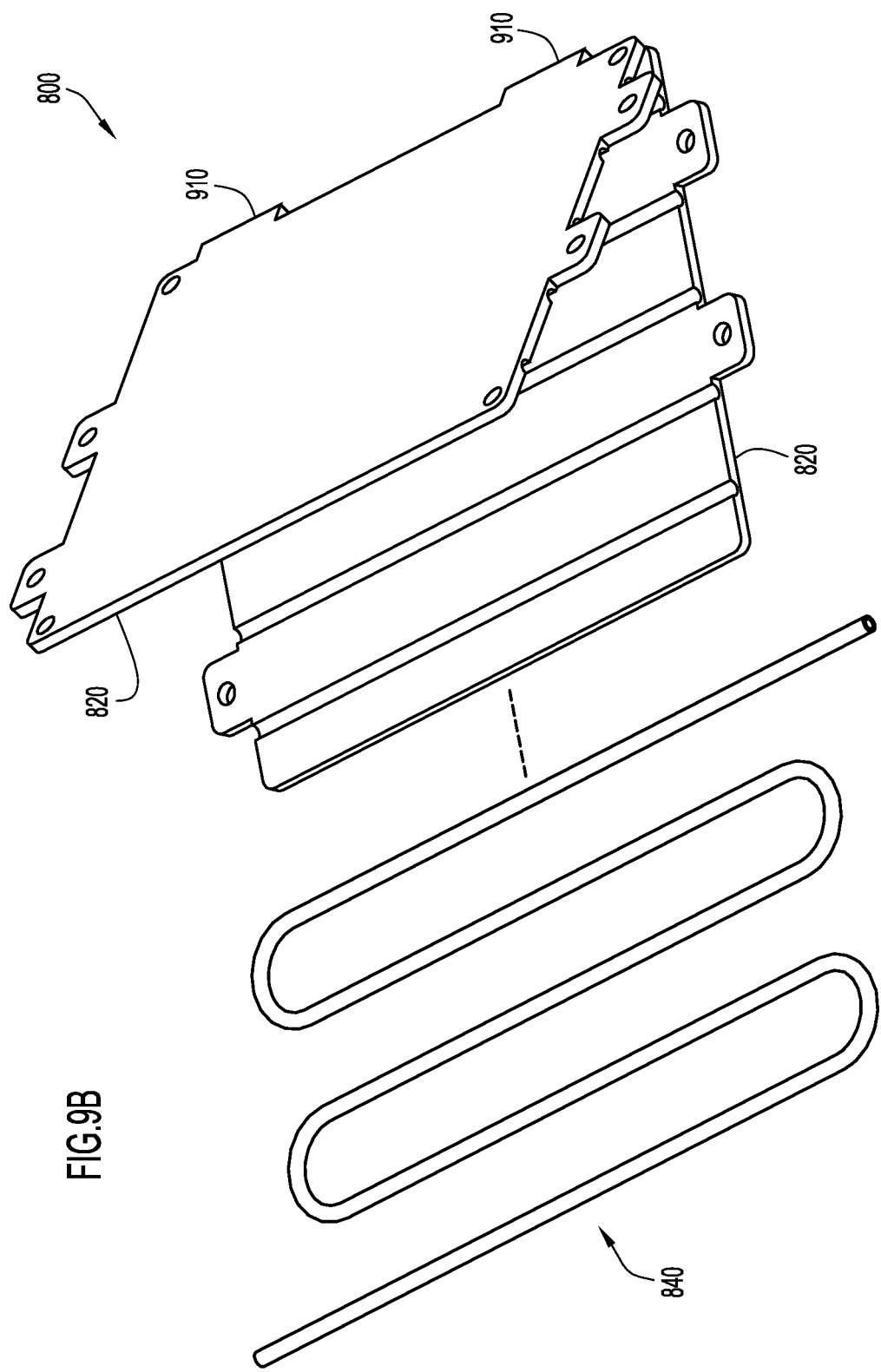
FIG. 9B is an exploded view in perspective of the warming device cartridge of FIG. 8 in a pivotable configuration according to an embodiment of the present invention.

Alternatively, cartridge 800 may be configured with heating plates 820 arranged for manipulation relative to each other as illustrated, by way of example, in FIG. 9B. In particular, cartridge 800 may include upper and lower heating plates 820 each coupled to a hinge or other pivoting mechanism 910. The hinges are disposed proximate a corresponding rear edge of each heating plate (e.g., as viewed in FIG. 9B). The hinges may be implemented by any quantity of any conventional or other hinges or pivoting mechanisms (e.g., hinge, bracket, etc.), and may be disposed at any suitable location. Heating plates 820 are arranged with their interior surfaces in facing relation. In this case, hinges 910 enable heating plates 820 to be manipulated or pivoted toward and away from each other. The heating plates, via hinges 910, may be manipulated away from each other, thereby transitioning the cartridge to an open state and enabling insertion and removal of conduit 840 from grooves 832 of the lower heating plate. Moreover, the heating plates may be manipulated toward each other, thereby transitioning the cartridge to a closed state and securing conduit 840 within the conduit channels formed by the combination of grooves 832 from each heating plate.

Warming unit 700 may be utilized with any types of infusion systems, and may include various warming devices to thermally treat medical fluids flowing therein. For example, the warming unit may be utilized with a basic administration set (e.g., with or without warming capability). In this case, the administration set includes a fluid source and tubing with the warming unit disposed along the tubing at any desired location (e.g., preferably toward the patient) to heat fluid flowing within the tubing. In addition, various warming device configurations may be employed to thermally treat cartridge 800 and fluid flowing therein.

Figure 10:
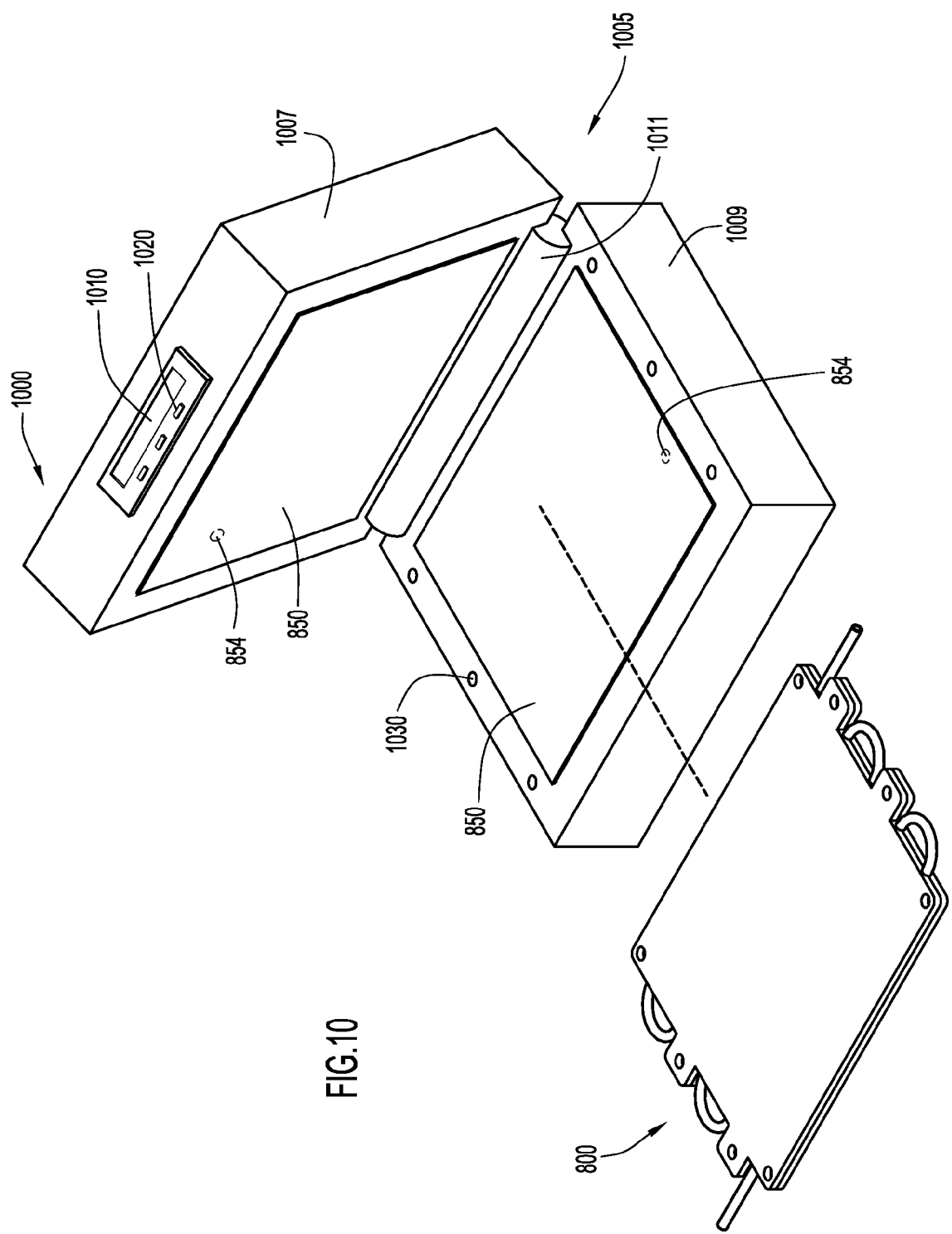
FIG. 10 is an exploded view in perspective of a warming device to receive the cartridge of FIG. 8 according to an embodiment of the present invention.

An example warming device for thermally treating fluids flowing within cartridge 800 is illustrated in FIG. 10. Specifically, warming device 1000 includes a housing 1005 including upper and lower housing members 1007, 1009. Each housing member is in the form of a substantially rectangular block and includes top, bottom, front, rear, and side walls. The upper and lower housing members are preferably connected along corresponding adjacent rear wall edges via one or more hinges or other pivoting mechanisms 1011 to enable the upper and lower housing members to be manipulated relative to each other. Upper housing member 1007 includes heating pad 850 and corresponding high limit temperature sensor 854. The heating pad provides thermal energy, while the high limit temperature sensor may be mounted on or proximate the heating pad to measure temperature of heating pad 850 and facilitate disablement of the heating pad in response to excessive measured temperatures. A display 1010 and corresponding input devices 1020 are preferably disposed on the front wall of upper housing member 1007. The input devices enable entry of a desired or set point temperature or range for fluid within cartridge 800, while the display provides the measured and desired or set point temperatures for the fluid within cartridge 800.

Lower housing member 1009 includes heating pad 850 and corresponding high limit temperature sensor 854. The heating pad provides thermal energy, while the high limit temperature sensor may be mounted on or proximate the heating pad to measure temperature of heating pad 850 and facilitate disablement of the heating pad in response to excessive measured temperatures. In addition, lower housing member 1009 includes one or more temperature sensors 1030 to measure temperature of fluid within cartridge 800. Heating plates 820 of cartridge 800 are preferably disposed within warming device 1000 substantially coincident heating pads 850 of the upper and lower housing members. Curved portions 846 of conduit 840 extend beyond the side edges of the heating plates and beyond the confines of the heating pads. Temperature sensors 1030 are preferably disposed proximate the curved sections of the conduit to measure temperature of the conduit, thereby providing a temperature indication for fluid flowing therein. The temperature measurements from temperature sensors 1030 may be combined in any desired fashion to provide a temperature measurement for the fluid within cartridge 800 (e.g., greatest or lowest temperature, average temperature, etc.). The measured temperature is provided to display 1010 for presentation to a user. Temperature sensors 1030 may be implemented by any quantity of any conventional or other temperature sensing device (e.g., RTD, IR, NTC, thermistor, thermocouple, etc.), and may be disposed at any locations within the upper and/or lower housing members. In addition, temperature sensors 1030 may be disposed on cartridge 800 (e.g., on heating plates 820, etc.) proximate conduit 840 and coupled to warming device 1000 to provide temperature measurements. The temperature sensors are isolated from the heating pad and in direct contact with or proximate conduit 840 to provide a temperature for fluid flowing therein.

Heating pads 850 are arranged in facing relation within the upper and lower housing members. In this case, hinges 1011 enable the upper and lower housing members to be manipulated or pivoted toward and away from each other. The upper and lower housing members, via hinges 1011, may be manipulated away from each other, thereby transitioning warming device 1000 to an open state and enabling insertion and removal of cartridge 800 from warming device 1000. Moreover, the upper and lower housing members may be manipulated toward each other, thereby transitioning the warming device to a closed state and securing cartridge 800 within warming device 1000 between heating pads 850 for thermal treatment of the cartridge and fluid therein.

Figure 11:
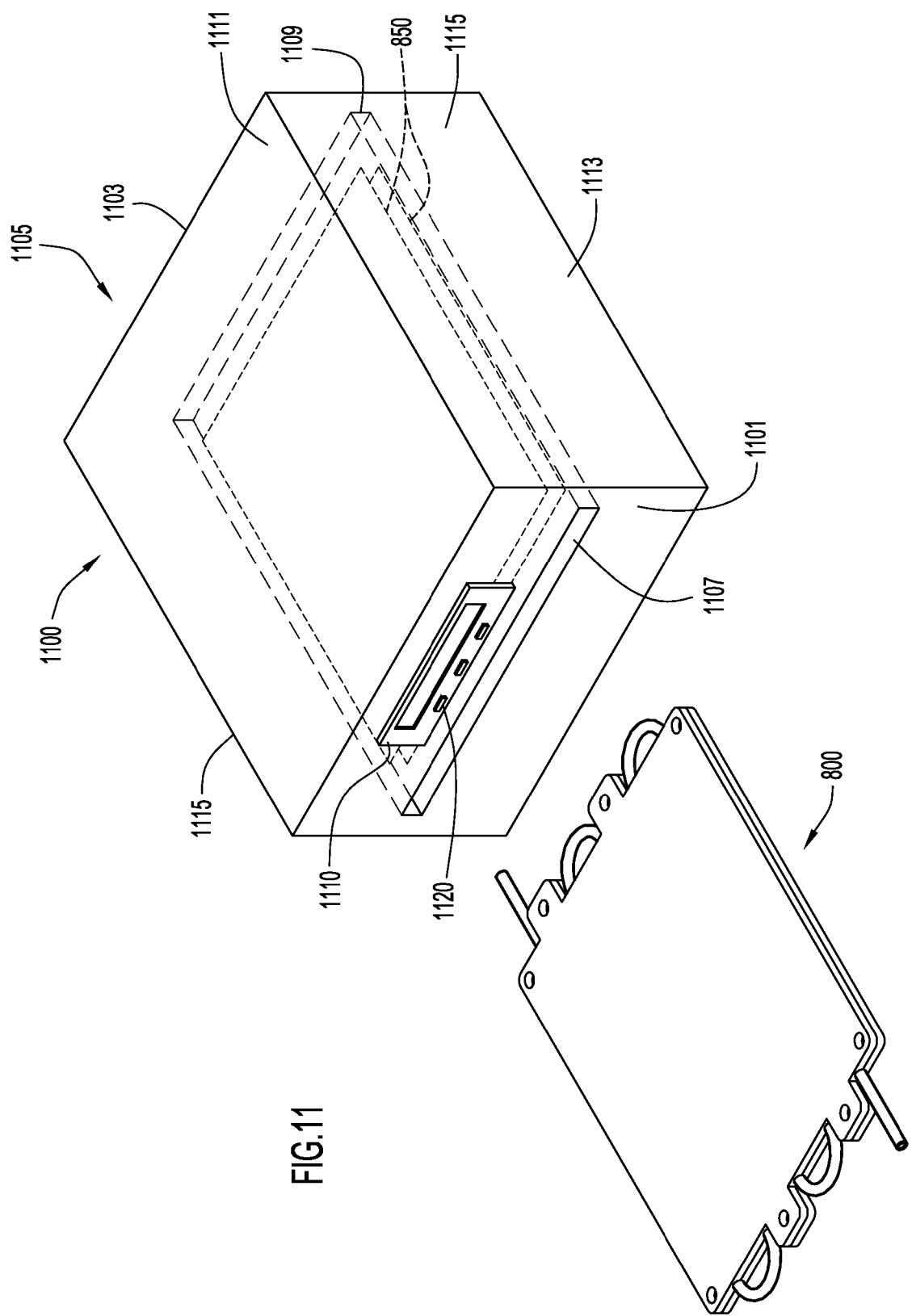
FIG. 11 is an exploded view in perspective of an alternative warming device to receive the cartridge of FIG. 8 according to an embodiment of the present invention.

An alternative warming device for thermally treating fluids flowing within cartridge 800 is illustrated, by way of example, in FIG. 11. In particular, warming device 1100 includes a housing 1105 in the form of a substantially rectangular block. The housing includes front wall 1101, rear wall 1103, top wall 1111, bottom wall 1113, and side walls 1115. The front and rear walls each include respective slots 1107, 1109 to facilitate insertion and removal of cartridge 800 within housing 1105. The slots include dimensions greater than those of cartridge 800, and are substantially rectangular. However, the slots may be of any shape and disposed at any desired locations on the housing. Housing 1105 includes a heating pad 850 and corresponding high limit temperature sensor 854 disposed toward each of the top and bottom walls. The heating pad provides thermal energy, while the high limit temperature sensor may be mounted on or proximate a corresponding heating pad to measure temperature of that heating pad and facilitate disablement of the heating pads in response to an excessive measured temperature. A display 1110 and corresponding input devices 1120 are preferably disposed on front wall 1101. The input devices enable entry of a desired or set point temperature or range for fluid within cartridge 800, while the display provides the measured and desired or set point temperatures for the fluid within cartridge 800.

In addition, housing 1105 includes one or more temperature sensors 1030 disposed therein to measure temperature of fluid within cartridge 800. Heating plates 820 of cartridge 800 are preferably disposed within warming device 1100 substantially coincident heating pads 850. Curved portions 846 of conduit 840 extend beyond the side edges of the heating plates and beyond the confines of the heating pads. Temperature sensors 1030 are preferably disposed within housing 1105 proximate the curved sections of the conduit to measure temperature of the conduit, thereby providing a temperature indication for fluid flowing therein. The temperature measurements from temperature sensors 1030 may be combined in any desired fashion to provide a temperature measurement for the fluid within cartridge 800 (e.g., greatest or lowest temperature, average temperature, etc.). The measured temperature is provided to display 1110 for presentation to a user. Temperature sensors 1030 may be implemented by any quantity of any conventional or other temperature sensing device (e.g., RTD, IR, NTC, thermistor, thermocouple, etc.), and may be disposed at any locations within housing 1105. In addition, temperature sensors 1030 may be disposed on cartridge 800 (e.g., on heating plates 820, etc.) proximate conduit 840 and coupled to warming device 1100 to provide temperature measurements.

Heating pads 850 are arranged in facing relation within the housing, where cartridge 800 is inserted through slot 1107 of front wall 1101 and between the heating pads within housing 1105 for thermal treatment. The cartridge may be withdrawn from housing 1105 via slot 1109 of rear wall 1103.

Figure 12:
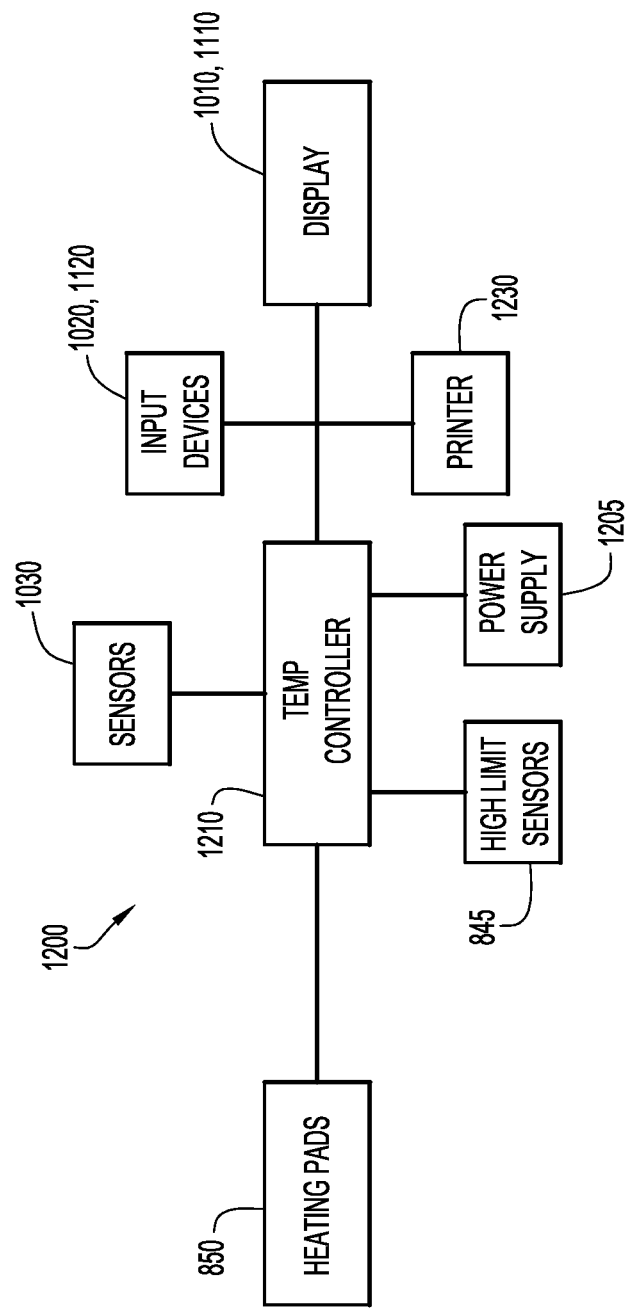
FIG. 12 illustrates an electrical schematic diagram of an example control circuit for the warming device of FIGS. 10 and 11.

An example control circuit for warming devices 1000, 1100 to control device operation is illustrated in FIG. 12. In particular, control circuit 1200 includes a temperature controller 1210, temperature sensors 1030 and high limit temperature sensors 854, heating pads 850, display 1010, 1110, input devices 1020, 1120, and a printer 1230. Temperature controller 1210 is connected to a power supply 1205. Power may be supplied from a common wall outlet jack via a power supply cord. Power may alternatively be supplied from a power source (e.g., a battery, etc.). This enables the warming device to be portable for use in the field for various applications (e.g., EMT applications, battlefield, etc.). In this case, warming devices 1000, 1100 may be water resistant or weatherproofed for outdoor use. Temperature controller 1210 is capable of measuring time to provide reports of solution temperature. The temperature controller is connected to high limit temperature sensors 854, temperature sensors 1030, and heating pads 850. In addition, temperature controller 1210 may further be coupled to printer 1230, input devices 1020, 1120, and display device 1010, 1110.

Temperature controller 1210 controls power to each heating pad 850 based on a temperature measurement of that heating pad via corresponding high limit temperature sensor 854. The high limit temperature sensor provides a temperature indication of the corresponding heating pad to the temperature controller. Temperature controller 1210 disables power to heating pads 850 in response to the measured temperature of one or more high limit temperature sensors 854 exceeding a predetermined excessive threshold temperature for the heating pad (e.g., a measured heating pad temperature exceeding 44° C. or other desired threshold temperature). In effect, this arrangement serves as a shut-off safety device to disable the heating pads 850 in response to excessive heating pad temperatures. The heating pads may alternatively be controlled by respective individual controllers based on measured temperature values of various items (e.g., heating plates, heating pad, solution, etc.).

In addition, the temperature controller maintains the solution at a desired temperature that is entered by the user via input devices 1020, 1120. Desired temperature information may be sent from the input devices to temperature controller 1210. The input devices may be manipulated to control display device 1010, 1110 to facilitate display of time, temperature, or other information entered by the user. The input devices may further facilitate the printing of information processed by the control circuit. The temperature controller controls power supplied to the heating pads based upon a comparison of the measured solution temperature (e.g., provided to the temperature controller by temperature sensors 1030) and the desired temperature. When the measured solution temperature is below the desired temperature, the temperature controller maintains or enables power to heating pads 850. Conversely, if the measured solution temperature exceeds the desired temperature, the temperature controller disables power to the heating pads. In addition, the temperature controller may apply controls based on heat ramps/profiles (e.g., via look-up tables with predetermined control parameters based on time, temperature, and/or fluid flow rates). Thus, the temperature controller may maintain the solution within cartridge 800 at a desired temperature entered by the user by enabling or disabling (or otherwise controlling) power to the heating pads.

Temperature controller 1210 may further provide the temperature measurements to a temperature controller of temperature controlled infusion system 100 to control heating of the solution container within heating cabinet 30 in substantially the same manner described above.

Input devices 1020, 1120 may further facilitate entry of an excessive threshold temperature for the heating pads to control when the temperature controller enables or disables power to the heating pads. Specifically, the temperature controller may be connected to the input devices to facilitate a comparison of the heating pad temperature measured by high limit temperature sensors 854 and the excessive threshold temperature for the heating pad entered by the user in order to determine whether to shut off power to the heating pads. The temperature controller may control any quantity of heating pads 850.

The temperature controller preferably includes a Peripheral Interface Controller (PIC) available from Microchip Technology, but may be implemented by or include any conventional or other controllers or microprocessors (e.g., chip, card, processor, circuitry, etc.) and receives various information (e.g., enablement of heating cabinet temperature, etc.) related to thermal treatment of the solution. The temperature controller may receive any additional information (e.g., facility information, doctor information, patient information, item (e.g., solution, instrument, etc.) information, etc.) from medical personnel or users via the input devices.

The temperature controller may further be configured to track/maintain parameters such as the date, elapsed heating time and occurrence time of an event or condition (e.g., the time when medical solutions are inserted and/or removed from the system, etc.). The temperature controller may measure the elapsed time or record an occurrence time. For example, the temperature controller may initiate measurement of a time interval in response to enablement of the heating, and may store the elapsed and/or occurrence time in response to any condition (e.g., when solution reaches the desired temperature). The temperature controller may further measure elapsed time or record elapsed and/or occurrence time in response to medical personnel manually entering information on the input devices (e.g., start and stop keys).

The temperature controller may be configured to collect the appropriate information and to arrange the information into a report. The report may be arranged in any fashion and include any desired information. Moreover, the report and/or information may be stored in a memory device (e.g., local controller memory, removable memory, card, disk, etc.) for later retrieval as described below. In addition, the temperature controller is coupled to display 1020, 1120 to display the elapsed (or running) time, report or any desired information to medical personnel. The information displayed may be selected via the input devices. The report may further be printed via printer 1230. The printer and display may be implemented by any conventional or other printer and/or display devices.

The temperature controller memory is used to store the collected information. Basically, the temperature controller logs records containing system information (e.g., the date/time that medical solution is heated, the date/time that the medical solution is removed from the system, temperatures, etc.). In this manner, use of the system is documented with recorded log entries. Log triggering events can be user defined via the input devices that allow the system to be configured to record information in response to a wide variety of detected conditions, continuously, and/or at particular times or periodic intervals. The memory can be used to store a wide variety of information related to use of the system and the memory may alternatively be implemented by an electronic memory chip, a smart card, a floppy disk, a fixed or removable magnetic disk. The temperature controller may be configured to support one or more of those memory storage types.

The information collected and/or recorded by the temperature controller and produced in a report can include, but is not limited to: the date/time that a medical solution was heated, the initial temperature of the medical solution, the temperature of the medical solution at specific points in time, start date and time that the medical solution began to be heated, the length of time that the medical solution was heated, the temperature that the medical solution was heated to during the heating cycle and/or the amount of solution or other item residing, placed in or removed from the system. The report may also include related information, such as patient information (e.g., name and identification number), facility information (e.g., name and location), doctor information, the type of procedure, the type of solution or other item being heated, the amount or quantity of fluid or other item being heated (e.g., fluid (or other item) level, volume or weight), the flow rate of fluid that is being heated, the temperature of fluid within the fluid line as the fluid is being infused, the pressure of fluid flow as the fluid is heated and any other desired information.

The system may employ any type of sensors or sensing devices (e.g., temperature sensors, presence sensors, weight sensors, volume sensors, pressure sensors, flow sensors, fluid sensors, fluid level sensors, etc.) to measure and provide any desired information to the temperature controller for inclusion in a report. The recordation or collection may occur automatically or via user entered information (e.g., start, stop and/or record keys) as described above.

The temperature controller stores and retrieves information from memory in order to produce a report. The report may be transmitted to printer 1230 that is disposed within the warming devices. The report may further be displayed by the warming device display. The printer basically provides a report in hardcopy form. The temperature controller may control the printer to produce the report at specified times (e.g., termination of heating, at particular times of day, after a particular quantity of uses, etc.) or in response to requests from medical personnel via input devices (e.g., print key). The printer may print the report on any desired hardcopy medium. The printer may place the information onto a label that is attached to a medical file. The information may be printed during or after the solution heating, or be stored on a memory device and printed at a desired time as described above. The printer may further provide additional copies of the report in response to user requests, or a medium automatically creating duplicates may be utilized (e.g., carbon-less paper, etc.).

The report may alternatively be provided in electronic form. The temperature controller may facilitate communication with other devices for transference or downloading of the report to those devices. For example, the information may be downloaded or transmitted over a network or other communications medium to another device (e.g., PDA, computer, another warming system, etc.) for viewing, storage and/or printing.

Information is collected by the temperature controller and stored in memory, typically in real-time, as events occur. Reports can be generated and printed/displayed in a timely manner to allow a local or remote (e.g., at a network workstation or computer) user to monitor the status of one or more systems and the status of medical solution undergoing thermal treatment. Alternatively, reports can be generated and printed/displayed at a time of a user choosing. For example, a user either local to or remote from a system is able to monitor the temperature of medical solutions and the time that medical solutions have been stored within a system based upon reports printed or shown on a display device. The user may access stored information relating to one or more systems by requesting (e.g., via temperature controller input devices, a remote workstation, etc.) that a report be produced or displayed to a specific printer or display (e.g., local or remote).

Operation of the warming unit is described with reference to FIGS. 8, 10, and 11. Initially, the warming unit may be utilized with any type of infusion system (with or without the capability to warm medical solutions inline or within a solution container) including a solution source and tubing to transport the solution from the source to a patient. Conduit 840 is initially sterilized and secured within cartridge 800 between heating plates 820 as described above. The cartridge is inserted into and secured with a warming device (e.g., warming device 1000, 1100), where each end of conduit 840 is attached to a corresponding portion of a fluid line at any desired location (e.g., preferably toward the patient) via a suitable Luer or other connector. A desired set point temperature or range is entered into the warming device via the input devices.

As fluid flows into and through conduit 840, heating pads 850 apply thermal energy to heating plates 820 of the cartridge. The thermal energy is subsequently applied by the heating plates to conduit 840 (and fluid flowing therein) residing within grooves 832 of the heating plates. The heating pads are controlled by temperature controller 1210 based on the temperatures measured by temperature sensors 1030 to heat the fluid to the desired temperature. In addition, the temperature controller disables power to the heating pads in response to a high limit temperature sensor indicating excessive temperatures.

While the present invention has been described in detail and with reference to specific embodiments thereof, it will be apparent to one skilled in the art that various changes and modifications can be made therein without departing from the spirit and scope thereof. For example, the heating and power supply cabinets may be of any shape or size, and may be constructed of any suitable materials. The cabinets may include housing walls, panels, ledges, projections and/or other structural components that may be of any quantity, shape or size, may be constructed of any suitable materials, and may be attached or connected via any suitable techniques (e.g., fasteners, welding, formed as integral components, etc.). Any number of hook members having any suitable shapes and dimensions may be disposed at any suitable locations on the heating plate or the heating cabinet housing for affixing solution containers in position with the heating plate. Each of the heating and power supply cabinets may further be supported on any type of support structure (e.g., IV or other pole, wall, counter, etc.) and may include any quantity of handles disposed at any suitable locations for facilitating portability. The cabinets may be positioned in any desired orientation for system operation. The support members of the heating and power supply cabinets may be of any suitable type and may have any suitable configuration to facilitate selective orientation of the cabinets with respect to the support structure to which they are secured. The heating and power supply cabinets may include any quantity of any conventional or other cord retracting mechanisms to retract and/or store any system cords (e.g., power supply cord, wall outlet cord, etc.). The retractor mechanisms may be disposed at any suitable locations on and/or within the cabinets.

The cover of the heating cabinet may be of any shape or size and may be constructed of any suitable materials (e.g., flexible, rigid, etc.). The cover is preferably constructed of transparent materials to permit clear viewing of the solution bag, but may alternatively be constructed of any translucent or opaque materials, or any combination of transparent, translucent and opaque materials. Any portion of the cover may be secured to the heating cabinet housing at any locations via any conventional or other fastening techniques (e.g., bolts, screws, adhesives, etc.). Further, any conventional or other fasteners (e.g., hook and loop, hooks, clasps, etc.) may be utilized to removably secure the cover to the heating cabinet housing. The cover may be disposed on the heating cabinet housing in any fashion and open from any direction (e.g., top, bottom, side, etc.) to removably secure the solution bag to the housing. Alternatively, the heating cabinet housing may include a roller type device to engage the cover unsecured end and wind the cover about the roller to retain the solution bag.

The cover may include any quantity of any type of conventional or other heating device (e.g., heating pad, acrylic heater, coils, etc.) to facilitate heating of the solution bag or container. The heating element wiring may be embedded within or disposed on the sheet and/or cover in any fashion and include any configuration suitable to heat the solution bag or container. The terminals may be of any quantity, shape or size, and may be embedded within or disposed on the sheet and/or cover at any suitable locations. The heating element may be formed integral with the cover.

The system may include any combination of heating plates, heating pads and/or heating elements. For example, the system may include any number of heating plates, heating pads and/or heating elements to heat one or more solution bags engaged with the heating cabinet to a desired temperature. The heating plate may include any quantity of heating panels of any shape or size and constructed of any suitable materials. The heating panels may be arranged in any fashion to form any type of heating plate configuration. The heating plate may include any quantity of conventional or other heating devices (e.g., heating pads, resistive wires, etc.) of any shape or size disposed at any suitable locations on the heating plate. The temperature sensors may be implemented by any quantity of any conventional or other type of temperature measuring devices disposed at any suitable locations for measuring the temperature of the heating plate and the solution container or containers engaging the heating cabinet. The system may heat and maintain the solution within the container to any desired temperature or range of temperatures.

The system control circuit may be arranged and disposed in the heating and/or supply cabinets in any fashion, and may include any conventional or other types of fuses (e.g., for any suitable current limit), controllers, switches (e.g., lighted), power supplies and other components. The controllers may each be implemented by any quantity of any conventional or other type of controller, microprocessor, or circuitry capable of collecting the report information for generating the reports and controlling the heating plate, heating element and/or temperature display. Alternatively, the controllers may be implemented by a commercially available controller pre-programmed and loaded with its own software. The controllers may be disposed at any suitable locations on or within the heating and power supply cabinets and include any types of displays, lights or other indicators, or switches (e.g., lighted) arranged in any fashion. Any number of temperature displays may be disposed at any locations on the heating cabinet and/or power supply cabinet and/or be remote from the system and may be implemented by any quantity of any conventional or other types of displays, such as LED or LCD displays. The heating controller and/or the temperature controller may be configured to directly control the heating plate and heating element in response to the measured temperatures and temperatures entered by the user, and disable the heating plate in response to excessive temperatures. The temperature display may display any quantity of digits and/or characters to reflect the actual and set point temperatures or any other desired information. The controllers may include any quantity of any types of input devices (e.g., buttons, keypad, voice recognition, etc.) disposed at any suitable locations on the heating cabinet and/or power supply cabinet to facilitate entry of information and/or selective control of the displays to display any desired information (e.g., desired temperature, actual temperature, temperature limit for the heating plate, etc.).

The power supplies may be implemented by any quantity of conventional or other type of power supply and provide power or voltage signals at any desired levels. The temperature control features of the present invention may be utilized individually and/or in any combination in response to system power and/or actuation of any quantity of any types of switches.

The heating cabinet may be configured to accommodate any quantity of solution bags or other containers of any shape or size. The heating cabinet may further be configured to include any suitable pressure device (e.g., a pressure device similar to the device described in U.S. Pat. No. 6,824,528) to provide pressurized infusion of fluid in combination with maintaining the solution container at a desired temperature. The bellows or bladder may be implemented by any inflatable device capable of expanding upon inflation, and may be inflated via any type of fluid, such as a gas (e.g., air) or liquid. The fluid may be heated in order to inflate the bellows and heat the solution bag. The bellows may be of any shape or size capable of applying pressure to the solution bag, may be constructed of any suitable materials, and may be disposed at any location and/or oriented in any fashion on the cover or within the housing. For example, the bellows may be disposed behind the heating plate and expand to force the heating plate against the solution bag to warm the solution and initiate a desired solution flow rate. The heating plate is typically hinged in this arrangement to transition between expanded and collapsed states in response to inflated and deflated states of the bellows, respectively. Further, any quantity (e.g., at least one) of bellows may be utilized to apply pressure to the solution bag in substantially the same manner described above. The hose for directing fluid to and from the bellows may be implemented by any conventional or other type of hose or tube, may be of any size or shape, and may be constructed of any suitable materials. The gauge for measuring and displaying pressure may be implemented by any conventional or other type of gauge, may be of any size or shape, and may be disposed at any suitable location. The bellows may be inflated by any type of inflating device or pump including any type of valve or other device for controlling inflation and deflation of the bellows.

The control or power supply cabinet may be configured to simultaneously provide power to any selected number of heating cabinets. The heating and power supply cabinets may further be configured to be compatible and interchangeable with other cabinets of similar design to facilitate the mobility of the cabinets during system operation.

The heating plate may be of any shape or size, be constructed of any suitable materials and include any quantity of heating panels of any shape or size. The heating plate and/or heating panels may be arranged in any fashion to form any type of heating plate configuration. The heating plate may include any quantity of conventional or other heating devices (e.g., heating pads, resistive wires, etc.) of any shape or size disposed at any suitable locations on the heating plate. The temperature sensor may be implemented by any quantity of any conventional or other type of temperature measuring devices disposed at any locations on the heating plate. Alternatively, a temperature sensor may be disposed in contact with the solution bag to directly measure a solution temperature.

The systems described above may include devices to record any types of information relating to system operation for subsequent retrieval, analysis, display and reports (e.g., date and time of thermal treatment disablement and enablement, fluid level or use, temperature, etc.). The systems may employ any type of sensors or sensing devices (e.g., temperature sensors, presence sensors, weight sensors, volume sensors, pressure sensors, flow sensors, fluid sensors, fluid level sensors, etc.) to measure and provide any desired information to the temperature controller for inclusion in a report. The temperature controllers of the systems may maintain the date, elapsed heating time and/or occurrence time of any event or condition (e.g., time medical solution is inserted and/or removed within system, etc.). The temperature controllers may measure the elapsed time or record an occurrence time for any desired condition. The temperature controllers may maintain the time information internally or utilize any desired external circuitry (e.g., a timer, etc.). Further, a separate controller may be used for information collection and reports.

The temperature controllers may collect any desired information (e.g., start date and time of solution or other item heating, the time interval the solution or other item was heated, the temperature the solution or other item attained during heating, temperature of the solution or other item when the solution was removed from the system, amount or quantity of solution or other item residing, placed in or removed from the system, partial or complete history of time and solution or other item temperature measured at any desired time intervals, facility name and location, patient information, doctor information, type of procedure, type of solution, amount or quantity of solution or other item being heated, etc.) from any desired sources (e.g., user, memory device, another computer or device, etc.). The temperature and/or other sensors may be coupled to the temperature controllers either individually or in any combination or fashion.

The reports may be arranged in any fashion and include any desired information. The date, time and other information may be in any desired format (e.g., month, day and year, hours and minutes, text, numeric, icons, etc.). The report information may be arranged and/or presented (e.g., printed, displayed, etc.) in any desired formats (e.g., text, charts, graphs, columns, rows, tables, etc.) and in any order or arrangement. The graph may include any quantity of axes each associated with any desired information (e.g., time, temperature, etc.) in any desired scales or units (e.g., Celsius, Fahrenheit, etc.). The graphs may utilize any types of symbols or characters (e.g., dots, diamonds, dashes, alphanumeric characters, punctuation symbols, etc.) to indicate points on the graph. The graphs may indicate time, temperature or events (e.g., removal of solution, etc.) in any fashion. The reports may provide information (e.g., temperature, etc.) measured or collected continuously or at any desired preset or user specified time intervals (e.g., hours, minutes, seconds, etc.). The time intervals may be specified by a user via any input devices (e.g., input devices (e.g., keys, buttons, etc.), remote or local computer, etc.). The report and/or information may alternatively be stored in a local or remote database or memory device (e.g., local memory, removable memory, etc.) for later retrieval. The reports may include a pre-arranged format or may be programmable or selected by a user via input devices. The temperature displays of the systems may be of any quantity, shape or size, may be disposed at any location on or remote from the systems, may be implemented by any conventional or other displays (e.g., LED, LCD, etc.) and may display any desired information. The information displayed may be selected via controller input devices, or the display may include display controls (e.g., buttons, keys, etc.).

The printer of the systems may be implemented by any conventional or other printing device, may be local or remote, may serve any quantity of systems or other devices, and may produce reports on any desired medium (e.g., paper, labels, etc.). The heating cabinet may include a printer and/or display to provide information to a user. The slot for providing a hardcopy report may be defined at any suitable locations on or within the heating and/or power supply cabinets. The reports may be printed and/or displayed concurrently with system operation as report data is collected or at any specific time or in response to user entered information (e.g., a print command or key). The report may be printed at any desired time before, during or after system use, and may be retrieved from the system at any desired time or in any desired manner. The systems or temperature controllers may include any conventional or other communications device or module (e.g., modem, etc.) and may download or transfer an electronic form of the report to any desired device (e.g., PDA, computer, another system, etc.) at any specific time or in response to user entered information (e.g., transmit command or key). Systems may further be networked to enable retrieval of reports and/or information from a station coupled to the network. The printer and display may be disposed at any suitable locations on or remote from the systems. Alternatively, the systems may be implemented to generate reports without the printer and/or display. Any desired information may be transmitted between the system components (e.g., temperature controller, printer, display, etc.) via any conventional or other communications medium or protocols (e.g., hardwire, wireless, network, etc.).

Software for the temperature, heating and report controllers may be implemented in any desired computer language and could be developed by one of ordinary skill in the computer arts based on the functional descriptions contained herein. The temperature, heating and report controllers may be implemented by any type of processors, hardware and/or other processing circuitry, and may be available pre-programmed for immediate use. The various functions of the temperature and heating controllers may be distributed in any manner among any quantity of software and/or hardware modules, processors and/or circuitry.

The power supply and heating cabinets may be formed as a single or integral unit, or be distributed among any quantity of units. Further, any conventional or other types of coupling devices or media (e.g., cables, wires, wireless, etc.) may be used to couple the cabinets or units or the components thereof.

The cartridge may be of any shape or size, and may be constructed of any suitable materials. The cartridge may include any number of heating plates, heating pads and/or heating elements to heat fluid within the cartridge. The heating plates may include any quantity of any types of grooves, apertures, channels, projections or other deformities of any shapes or sizes. The heating plates may be constructed of any suitable thermally conducting material (e.g., aluminum, metal, types of plastic, etc.). The cartridge may be utilized within any devices that thermally treat (e.g., heat and/or cool) the fluid. The heating plates may be arranged in any orientation, where either heating plate may receive the conduit. The fasteners may include any quantity of any conventional or other fasteners to removably secure the heating plates (e.g., bolt, screw, clips, etc.). The hinges or pivoting mechanisms may include any quantity of any conventional or other pivoting devices (e.g., hinge, joint, bracket, etc.) to enable the heating plates to be manipulated relative to each other.

The conduit may be of any shape or size, and may be constructed of any thermally conductive materials (e.g., stainless steel or other metals, materials with metallic type properties, types of plastic, etc.). The tubular member may include any quantity of sections to form any desired flow path or configuration (e.g., circular, spiral, serpentine, etc.). The linear sections may be linear or angled or curved in any fashion, while the curved sections may be include any degrees of curvature.

The housings of the warming devices may include housing walls, panels, ledges, projections and/or other structural components that may be of any quantity, shape or size, may be constructed of any suitable materials, and may be attached or connected via any suitable techniques (e.g., fasteners, welding, formed as integral components, etc.). The upper and lower housing members may similarly be of any quantity, shape, or size, and may be constructed of any suitable materials. The hinges or pivoting mechanisms may include any quantity of any conventional or other pivoting devices (e.g., hinge, joint, bracket, etc.) to enable the upper and lower housing members to be manipulated relative to each other. The components (e.g., heating pads, temperature sensors, etc.) of the warming devices may be disposed and arranged within the housing or any of the housing members in any desired fashion. The slots may be of any quantity, shape or size, and may be disposed at any locations of the warming device housing. The temperature sensors and high limit temperature sensors may be may be implemented by any quantity of any conventional or other type of temperature measuring devices disposed at any suitable locations for measuring the temperature of the heating plate, heating pad, conduit and/or fluid. The excessive temperature and set point temperature may be set to any desired values (e.g., excessive temperature preferably greater than 40° C. for heating to body temperature, temperature range approximately 36°-40° C. for heating to body temperature, etc.) appropriate for the fluid and/or application. The heating pads may be of any quantity, shape or size, may be disposed at any desired locations within the housings to heat the heating plates, and may be implemented by any conventional or other types of heating elements (e.g., pads, coils, wires, etc.).

The control circuit for the warming devices may be arranged and disposed in the housings in any fashion, and may include any conventional or other types of controllers, power supplies and other components. The temperature controller may be implemented by any quantity of any conventional or other type of controller, microprocessor, or circuitry capable of collecting the report information for generating the reports and controlling the heating pads and temperature display. Alternatively, the temperature controller may be implemented by a commercially available controller pre-programmed and loaded with its own software. The controller may be disposed at any suitable locations on or within the housings of the warming devices and include any types of displays, lights or other indicators, or switches (e.g., lighted) arranged in any fashion. Any number of temperature displays may be disposed at any locations on the housings and/or be remote from the warming devices and may be implemented by any quantity of any conventional or other types of displays, such as LED or LCD displays. The temperature display may display any quantity of digits and/or characters to reflect the actual and set point temperatures or any other desired information. Any quantity of any types of input devices (e.g., buttons, keypad, voice recognition, etc.) may be disposed at any suitable locations on the housings to facilitate entry of information and/or selective control of the displays to display any desired information (e.g., desired temperature, actual temperature, temperature limit for the heating plate, etc.). The control circuit may utilize any suitable power source (e.g., wall outlet jack, batteries or other portable power sources, etc.).

The present invention is not limited to the applications disclosed herein, but may be utilized for infusion of any fluids (e.g., saline, blood, antibiotics or other drugs, gases, irrigation fluids, etc.).

Thus, it is intended that the present invention covers various modifications and variations of this invention. It is to be understood that terms such as "top", "bottom", "front", "rear", "side", "height", "length", "width", "upper", "lower", "interior", "exterior", and the like as may be used herein, merely describe points of reference and do not limit the present invention to any particular orientation or configuration.

Having described preferred embodiments, it is believed that other modifications, variations and changes will be suggested to those skilled in the art in view of the teachings set forth herein. It is therefore to be understood that all such variations, modifications and changes are believed to fall within the scope of the present invention. Although specific terms are employed herein, they are used in a generic and descriptive sense only and not for purposes of limitation. An embodiment of the present invention may be summarized as follows: A temperature sensing device for measuring temperature of a sterile medical fluid comprising a medical fluid container to house a sterile medical fluid; a fitting disposable at a selected location along a fluid conduit, the conduit configured to direct said medical fluid toward a patient; and at least one thermal treatment device securable to a selected location on said fitting operable to thermally treat said sterile medical fluid. The device may further include a temperature sensor to measure temperature of said sterile medical fluid flowing through said fitting and to generate an electrical temperature signal indicating said measured fluid temperature, as well as a controller coupled to said temperature sensor and said at least one thermal treatment device to control said at least one thermal treatment device to thermally treat said medical fluid to a desired temperature.

The fitting, moreover, may further include a first open end and a second open end, each end being securable to selected portions of said fluid line and a passage disposed within said fitting to permit said sterile medical fluid flowing within said fluid line to flow through said fitting.

Another embodiment of the present invention may be summarized as a thermal treatment unit for controlling temperature of a sterile medical fluid. The unit comprises a thermal treatment device and a cartridge. The thermal treatment device is disposable at a selected location along a fluid line that is configured to direct the medical fluid toward a patient. The cartridge is configured for insertion within the thermal treatment device and includes a conduit to receive and thermally treat fluid from the fluid line within the thermal treatment device. The conduit is removable from the cartridge for sterilization.

We claim:

1. A temperature sensing system for measuring temperature of a sterile medical fluid, the temperature sensing device comprising:
    a medical fluid line configured to couple to a medical fluid container housing a sterile medical fluid, the medical fluid line receiving the sterile medical fluid from the medical fluid container and directing the sterile medical fluid downstream toward a patient;
    a fitting coupled to the medical fluid line such that the fitting at least partially surrounds the medical fluid line, the fitting permitting the passage of fluid downstream to the patient, and
    a sensor housing mounted on the fitting at a first location, the sensor housing including a first side, a second side, first temperature sensor to indicate a first measured temperature and a second temperature sensor to indicate a second measured temperature, wherein the second temperature sensor is disposed proximate to the second side of the sensor housing downstream from the first temperature sensor disposed proximate to the first side of the sensor housing; a thermal treatment device coupled to the fitting at a second location, the second location being disposed upstream from the first location, the thermal treatment device including at least one heating element and is operable to thermally treat the sterile medical fluid as it flows downstream from the medical fluid container; and
    a controller in communication with the first temperature sensor and the second temperature sensor, the controller operable to compare the first measured temperature to said second measured temperature to control the thermal treatment device to maintain the sterile medical fluid at a desired temperature.

2. The system of claim 1, wherein the controller is further in communication with the thermal treatment device, the controller engaging or disengaging the thermal treatment device in response to comparing the first measured temperature to the second measured temperature.

3. The system of claim 1, Wherein:
    the system further comprises an alerting device to notify a user of an abnormal condition;
    the controller is further in communication with the alerting device; and
    the controller engages the alerting device in response to comparing the first measured temperature to the second measured temperature.

4. The system of claim 1, wherein the controller determines a flow rate of the medical fluid through the temperature sensing device via comparison of the first measured temperature to the second measured temperature.

5. The system of claim 1, wherein:
    the system further comprises an alerting device to notify a user of an abnormal condition;
    the controller is further in communication with the alerting device; and
    the controller activates the alerting device when the second measured temperature is equal to or greater than the first measured temperature.

6. The system of claim 1, wherein:
    the sensor housing comprises a housing inlet disposed on the first side upstream from a housing outlet disposed on the second side;

the first temperature sensor is disposed proximate the housing inlet such the first measured temperature indicates temperature of the fluid proximate the housing inlet ($T_f$); and the second temperature sensor is disposed proximate the housing outlet such that the second measured temperature indicates temperature of the fluid proximate the housing outlet ($T_e$).

7. The system of claim 1, wherein:
the sensor housing further comprises:
  a body defining an exterior surface, and
  an interior channel proximate to the first side extending through the body;
the first sensor is mounted on the body interior channel; and
the second sensor is mounted on the body exterior surface proximate to the second side.

8. The system of claim 7, wherein:
the interior channel defines a housing inlet and a housing outlet, the housing outlet being located on the second side downstream from the housing inlet located on the first side;
the first sensor is disposed proximate the housing inlet such that the first measured temperature indicates a temperature of medical fluid proximate the housing inlet; and
the second sensor indicates ambient temperature.

9. The system of claim 7, wherein:
the system further comprises an alerting device to notify a user of an abnormal condition;
the controller is further in communication with said alerting device; and
the controller activates the alerting device if the second measured temperature is equal to or greater than the first measured temperature.

10. A method of measuring temperature of a sterile medical fluid flowing within a medical fluid line, the method comprising:
  directing a sterile medical fluid along a medical fluid line; and
  directing said sterile medical fluid through:
    a fitting coupled to the medical fluid line the fitting at least partially surrounding the medical fluid line and permitting the passage of the sterile medical fluid downstream to the patient directing said sterile medical fluid through a thermal treatment device coupled to the fitting at a first location, the thermal treatment device includes at least one heating element and is operable to thermally treat the sterile medical fluid at the first location as it flows downstream from a medical fluid container and toward a patient; and directing said sterile medical fluid through
    a sensor housing mounted on said fitting at a second location, the sensor housing including a first side, a second side, a first temperature sensor disposed on the sensor housing proximate to the first side to indicate a first measured temperature and a second temperature sensor disposed on the sensor housing proximate to the second side to indicate a second measured temperature the sensor housing further includes
    a controller in communication with the first temperature sensor and the second temperature sensor, the controller being operable to compare the first measured temperature to the second measured temperature to control the thermal treatment device to maintain the sterile medical fluid at a desired temperature,
the second temperature sensor is disposed downstream from the first temperature sensor.

11. The method of claim 10 further comprising:
measuring a first measured temperature via the first temperature sensor, the first measured temperature indicating a first temperature of the sterile medical fluid flowing within the inline conduit at a first conduit position proximate to the first side of the sensor housing;
measuring a second measured temperature, the second measured temperature indicating a second temperature of the sterile medical fluid flowing within the inline conduit at a second conduit position proximate to the second side of the sensor housing, the second conduit position being downstream from the first conduit position; and
comparing the first measured temperature to the second measured temperature.

12. The method of claim 11, wherein:
the sensor housing further includes an alerting device to alert a user of a condition;
the controller is in communication with the alerting device; and
the controller activates the alerting device when the second temperature is greater than the first temperature by a predetermined value.

13. The method of claim 10 further comprising:
measuring a first measured temperature via the first temperature sensor, the first measured temperature indicating a first temperature of the sterile medical fluid flowing within the inline conduit proximate to the first side of the sensor housing;
measuring a second measured temperature via the second temperature sensor, the second measured temperature indicating ambient temperature outside the conduit proximate to the second side of the sensor housing; and
comparing the first measured temperature to the second measured temperature.

14. The method of claim 13, wherein:
the sensor housing further includes an alerting device to alert a user of a condition;
the controller is in communication with the alerting device; and
the controller activates the alerting device when the second temperature is equal to the first temperature or is greater than the first temperature by a predetermined value.

* * * * *